US008588914B2

(12) United States Patent
Rooney et al.

(10) Patent No.: US 8,588,914 B2
(45) Date of Patent: Nov. 19, 2013

(54) IMPLANTABLE MEDICAL DEVICE WITH ELECTRODES ON MULTIPLE HOUSING SURFACES

(75) Inventors: Ethan A. Rooney, White Bear Lake, MN (US); Carl D. Wahlstrand, Lino Lakes, MN (US); Gary W. King, Fridley, MN (US); Thomas E. Cross, Jr., St. Francis, MN (US); Richard T. Stone, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 2241 days.

(21) Appl. No.: 11/450,127

(22) Filed: Jun. 9, 2006

(65) Prior Publication Data

US 2007/0073353 A1 Mar. 29, 2007

Related U.S. Application Data

(63) Continuation-in-part of application No. 11/374,852, filed on Mar. 14, 2006, now Pat. No. 7,813,803, and a continuation-in-part of application No. 11/375,492, filed on Mar. 14, 2006, now Pat. No. 7,890,166, and a continuation-in-part of application No. 11/374,793, filed on Mar. 14, 2006, now Pat. No. 8,244,360.

(60) Provisional application No. 60/689,202, filed on Jun. 9, 2005, provisional application No. 60/700,627, filed on Jul. 19, 2005, provisional application No. 60/761,823, filed on Jan. 25, 2006.

(51) Int. Cl.
*A61N 1/375* (2006.01)

(52) U.S. Cl.
USPC ........................................................ 607/36

(58) Field of Classification Search
USPC .................................................... 607/36–37
See application file for complete search history.

(56) References Cited

U.S. PATENT DOCUMENTS

| 3,211,151 A | 10/1965 | Foderick et al. |
| 3,385,300 A | 5/1968 | Holter |

(Continued)

FOREIGN PATENT DOCUMENTS

| DE | 19758114 | 7/1999 |
| GB | 2 274 995 | 8/1994 |

(Continued)

OTHER PUBLICATIONS

Kapural et al., "Occipital Nerve Electrical Stimulation via the Midline Approach and Subcutaneous Surgical Leads for Treatment of Severe Occipital Neuralgia: A Pilot Study," Anesthesia Analgesia 2005; 101, pp. 171-174.

(Continued)

*Primary Examiner* — Amanda Patton
(74) *Attorney, Agent, or Firm* — Shumaker & Sieffert, P.A.

(57) ABSTRACT

An implantable medical device (IMD) with a housing and electrodes on at least two surfaces of the housing is described. The surfaces may be, for example, opposed, substantially parallel surfaces, e.g., top and bottom surfaces. Location of electrodes on multiple surfaces of the housing may allow the IMD to deliver stimulation to a variety of tissues and with a variety of current field configurations. For example, the IMD may deliver peripheral nerve field stimulation (PNFS) to one or more tissue areas via electrodes selected from one or both of the surfaces to, for example, reduce the sensation of pain in a tissue area proximate to an implantation site of the IMD without targeting a specific nerve. The IMD may be implanted between or within intra-dermal, deep dermal, or subcutaneous layers of the tissue of the patient to deliver PNFS to any one or more of these layers.

29 Claims, 16 Drawing Sheets

(56) References Cited

U.S. PATENT DOCUMENTS

| | | | |
|---|---|---|---|
| 3,978,865 A | 9/1976 | Trabucco | |
| 4,058,128 A | 11/1977 | Frank et al. | |
| 4,142,530 A | 3/1979 | Wittkampf | |
| 4,177,818 A | 12/1979 | De Pedro | |
| 4,759,748 A | 7/1988 | Reed | |
| 5,300,110 A | 4/1994 | Latterell et al. | |
| 5,545,207 A | 8/1996 | Smits et al. | |
| 5,792,187 A | 8/1998 | Adams | |
| 5,954,757 A | 9/1999 | Gray | |
| 6,038,480 A | 3/2000 | Hrdlicka et al. | |
| 6,058,331 A | 5/2000 | King | |
| 6,249,707 B1 | 6/2001 | Kohnen et al. | |
| 6,473,653 B1 | 10/2002 | Schallhorn et al. | |
| 6,517,477 B1 | 2/2003 | Wendlandt | |
| 6,735,475 B1 | 5/2004 | Whitehurst et al. | |
| 6,941,171 B2 * | 9/2005 | Mann et al. | 607/39 |
| 6,978,180 B2 | 12/2005 | Tadlock | |
| 7,010,345 B2 | 3/2006 | Hill et al. | |
| 7,120,495 B2 * | 10/2006 | Bardy et al. | 607/36 |
| 2002/0103510 A1 | 8/2002 | Bardy et al. | |
| 2002/0107553 A1 | 8/2002 | Hill et al. | |
| 2002/0143369 A1 | 10/2002 | Hill et al. | |
| 2002/0165586 A1 | 11/2002 | Hill et al. | |
| 2002/0198572 A1 | 12/2002 | Weiner | |
| 2003/0004549 A1 | 1/2003 | Hill et al. | |
| 2003/0078633 A1 | 4/2003 | Firlik et al. | |
| 2003/0144709 A1 | 7/2003 | Zabara et al. | |
| 2003/0212445 A1 | 11/2003 | Weinberg | |
| 2004/0015204 A1 * | 1/2004 | Whitehurst et al. | 607/48 |
| 2004/0059348 A1 | 3/2004 | Geske et al. | |
| 2004/0098074 A1 | 5/2004 | Erickson et al. | |
| 2004/0122477 A1 | 6/2004 | Whitehurst et al. | |
| 2004/0172090 A1 | 9/2004 | Janzig et al. | |
| 2004/0176819 A1 | 9/2004 | Wahlstrand et al. | |
| 2004/0176830 A1 | 9/2004 | Fang | |
| 2004/0243205 A1 | 12/2004 | Keravel et al. | |
| 2005/0015117 A1 | 1/2005 | Gerber | |
| 2005/0070969 A1 | 3/2005 | Gerber | |
| 2005/0222628 A1 | 10/2005 | Krakousky | |
| 2005/0246006 A1 | 11/2005 | Daniels | |
| 2005/0256452 A1 | 11/2005 | DeMarchi et al. | |
| 2006/0030899 A1 | 2/2006 | O'Keeffe et al. | |
| 2006/0270978 A1 | 11/2006 | Binmoeller et al. | |
| 2007/0118196 A1 | 5/2007 | Rooney et al. | |

FOREIGN PATENT DOCUMENTS

| | | |
|---|---|---|
| WO | WO 01/89626 | 11/2001 |
| WO | WO 02/34330 | 5/2002 |
| WO | WO 02/068042 | 9/2002 |
| WO | WO 03/026736 | 4/2003 |
| WO | WO 03/047687 | 6/2003 |
| WO | WO 2004/012812 | 2/2004 |

OTHER PUBLICATIONS

Notification of Transmittal of the International Search Report and the Written Opinion for corresponding PCT Application No. PCT/US2006/02271.8, dated Jan. 23, 2007 (12 pgs.).

Reply to Written Opinion for corresponding PCT Application No. PCT/US2006/022718, dated Apr. 23, 2007 (8 pgs.).

Written Opinion for corresponding PCT Application No. PCT/US2006/022718, dated Jun. 28, 2007 (6 pgs.).

Reply to Written Opinion for corresponding PCT Application No. PCT/US2006/022718, dated Aug. 28, 2007 (11 pgs.).

Notification of Transmittal of the International Preliminary Report on Patentability for corresponding PCT Application No. PCT/US2006/022718, dated Sep. 26, 2007 (10 pgs.).

U.S. Appl. No. 11/450,133, filed Jun. 9, 2006, entitled "Combination Therapy Including Peripheral Nerve Field Stimulation."

U.S. Appl. No. 11/450,147, filed Jun. 9, 2006, entitled "Introducer for Therapy Delivery Elements."

U.S. Appl. No. 11/450,144, filed Jun. 9, 2006, entitled "Peripheral Nerve Field Stimulation and Spinal Cord Stimulation."

U.S. Appl. No. 11/450,148, filed Jun. 9, 2006, entitled "Implantable Medical Lead."

U.S. Appl. No. 11/374,852, filed Mar. 14, 2006, entitled "Regional Therapies for Treatment of Pain."

U.S. Appl. No. 11/375,492, filed Mar. 14, 2006, entitled "Regional Therapies for Treatment of Pain."

U.S. Appl. No. 11/374,793, filed Mar. 14, 2006, entitled "Regional Therapies for Treatment of Pain."

Office Action dated Sep. 8, 2009 for U.S. Appl. No. 11/450,148 (5 pgs.).

Responsive Amendment dated Dec. 8, 2009 for U.S. Appl. No. 11/450,148 (8 pgs.).

* cited by examiner

IMPLANTABLE MEDICAL DEVICE WITH ELECTRODES ON MULTIPLE HOUSING SURFACES

This application claims the benefit of U.S. Provisional Application No. 60/689,202, filed Jun. 9, 2005. This application is also a continuation-in-part of each of U.S. application Ser. Nos. 11/374,852, filed on Mar. 14, 2006, Ser. No. 11/375,492, filed on Mar. 14, 2006, and Ser. No. 11/374,793, filed on Mar. 14, 2006, each of which claims the benefit of U.S. Provisional Application Nos. 60/700,627, filed on Jul. 19, 2005, and 60/761,823, filed on Jan. 25, 2006. The entire content of each of these applications is incorporated herein by reference.

TECHNICAL FIELD

The invention relates to medical devices and, more particularly, to implantable medical devices that deliver electrical stimulation.

BACKGROUND

A variety of therapies, such as neurostimulation and pharmaceutical therapies, e.g., drugs, may be delivered to a patient to treat chronic or episodic pain. Examples of neurostimulation therapies used to treat pain are transcutaneous electrical nerve stimulation (TENS), percutaneous electrical nerve stimulation (PENS), peripheral nerve stimulation (PNS), spinal cord stimulation (SCS), deep brain stimulation (DBS) and cortical stimulation (CS). Examples of drugs used to treat pain are opioids, cannabinoids, local anesthetics, baclofen, adenosine and alpha-blockers.

PNS, SCS, DBS and CS are typically delivered by an implantable medical device (IMD). An IMD delivers neurostimulation therapy via electrodes, which are typically coupled to the IMD by one or more leads. The number and positions of the leads and electrodes is largely dependent on the type or cause of the pain, and the type of neurostimulation delivered to treat the pain. In general, an IMD delivers neurostimulation therapy in the form of electrical pulses.

SCS involves stimulating the spinal cord at specifically targeted locations, typically via leads and electrodes that are either surgically implanted post laminectomy, or inserted percutaneously. Delivering stimulation to the appropriate location on the spinal cord causes paresthesia that overlay the pain region to reduce the area of perceived pain. SCS can result in the patient experiencing paresthesia in a relatively large area, including more than one limb.

SCS has been shown to be effective for axial or longitudinal back pain, failed back surgery syndrome (FBBS), cervical pain, occipital nerve pain, supra-orbital pain, facial pain, inguinal and pelvic pain, and chest and intercostal pain. As examples, electrodes for SCS may be implanted in the epidural space near vertebral levels T8-T10 to treat axial back pain, over the dorsal columns at vertebral levels T10-L1 to treat pain in the back, legs, ankles or feet, or over the dorsal roots, i.e., proximal to the dorsal root entry zone, of vertebral levels L3-S1. SCS may be most effective for neuropathic pain, such as neuropathy or radiculopathy that involves a significant portion of one limb and more than one dermatome.

PNS is typically used to treat patients suffering from intractable pain secondary to nerve damage isolated to a single nerve. PNS places a group of electrodes in very close proximity to, e.g., in contact with, and approximately parallel to a major nerve in the subcutaneous tissue. PNS may also place a group of electrodes in very close proximity to a nerve that may be deeper in the limb, sometimes near to blood vessels. Placing electrodes in very close proximity to the nerve may ensure that only fibers within that nerve are activated at low amplitudes.

PNS electrodes may be located on percutaneous leads, but for stability and to prevent stimulation of other tissues proximate to the target peripheral nerve, PNS electrodes are generally located within insulative material that wraps around a nerve, i.e. cuff electrodes, or on one surface of a flat paddle of insulative material placed under a nerve. In any case, the electrodes for PNS are placed in close proximity to the nerve "upstream" from the source of damage or pain, e.g., closer to the spinal cord than the region of damage or pain. When electrodes are implanted upstream, the paresthesia resulting from PNS may extend to a broader area innervated by the target peripheral nerve. The most common upper extremity nerves treated with PNS are the ulnar nerve, median nerve, radial nerve, tibial nerve and common peroneal nerve.

DBS and CS can be used to treat neuropathic and nociceptive pain through delivery of stimulation to various structures of the brain. DBS may treat pain through delivery of stimulation to gray matter within the midbrain, or the thalamus, via electrodes implanted in the brain. CS may treat pain through delivery of stimulation to the sensory and/or motor cortex via electrodes placed in or on the cortex.

Drugs that treat pain may be delivered by an implantable pump, external pump, transdermally, or orally. Typically, an implantable pump delivers one or more drugs to a target location via a catheter. The target location may be intrathecal or extradural.

The pain experienced by a patient may be complex and/or multifocal. Complex or multifocal pain may include pain experienced by a patient at different locations of the body, pain attributable to different causes or pathologies, and/or pain of different types, e.g., neuropathic and/or nociceptive pain. For some patients with complex and/or multifocal pain, any one of the pain treatment modalities identified above may be unable to completely treat the experienced pain. For example, SCS may not adequately treat pain in a large number of cases, perhaps the majority, because it has been shown to help neuropathic, but not nociceptive, pain states. Nociceptive pains can come from pressure, inflammation, and temperature changes.

Further, over time, the nervous system of a patient may accommodate a particular treatment modality. Such neural accommodation may render a previously effective modality, or dose or intensity for the modality, ineffective. Neural accommodation may result from noxious sensations being rerouted to traverse alternative pathways in the nervous system that are not affected by the accommodated modality, at least at the current dose or intensity. Simply increasing the dose or intensity of a current modality to overcome accommodation may not be effective, or may be undesirable for a variety of reasons, such as increased battery or reservoir consumption, increased side-effects, or increased likelihood of chemical dependency.

SUMMARY

In general, the invention is directed to an implantable medical device (IMD) with a housing and electrodes located on at least two surfaces of the housing. The surfaces may be, for example, opposed and/or substantially parallel surfaces, e.g., a top surface and bottom surface. Location of electrodes on multiple surfaces of the housing may allow the IMD to deliver stimulation to a variety of tissues proximate to the IMD, and with a variety of current field configurations. In some embodiments, the IMD includes pulse generation circuitry, and delivers electrical stimulation in the form of pulses.

The one or more electrodes on each of two or more housing surfaces of the IMD may be formed on the surfaces as pad electrodes. The electrodes may generally be substantially flat electrode pads with a substantially circular cross-section, but may also have any two or three-dimensional shape. In some embodiments, the electrodes may be recessed into the housing, e.g., formed in recesses of the housing, such that they are substantially flush with the surface. In some embodiments, the IMD may include a housing with a low profile, e.g., a thin housing, which permits dermal or subcutaneous implantation in any of a variety of locations in the body of the patient.

In some embodiments, one or more of the housing surfaces may include a plurality of electrodes that are spatially distributed over substantially the entire surface. Distribution of electrodes over substantially the entire surface may provide flexibility in selecting electrodes, and thereby provide flexibility in selecting a location, size and shape of a current field resulting from delivery of stimulation by the IMD via the selected electrodes. However, any configuration of the electrodes on the surface is possible. For example, one or more rows of electrodes may be arranged along an axis of the surface, e.g., along major axis of the surface or the length of the surface, or electrodes may be grouped into one or more "clusters" on portions of a surface. An inter-electrode distance on the surface may be within a range from approximately 0.1 mm to 5.0 mm, and may be approximately 0.5 mm.

An IMD according to the invention may be used to deliver electrical stimulation to provide a variety of therapies. For example, the IMD may deliver peripheral nerve field stimulation (PNFS) to one or more tissue areas via electrodes selected from one or both of the surfaces to, for example, reduce the sensation of pain in a tissue area proximate to an implantation site of the IMD without targeting a specific nerve. For delivery of PNFS, the IMD with housing electrodes may be positioned, i.e., implanted, in the tissue of a patient within the region where the patient experiences pain. The IMD may be implanted within, for example, intra-dermal, deep dermal, or subcutaneous tissues of the patient. The PNFS current may spread along paths of lower resistance in any of numerous directions from electrodes, but generally spreads parallel to the skin surface. The PNFS current may spread over an area of several centimeters. PNFS is not delivered to a specific nerve.

Depending on the location at which the electrodes are implanted, PNFS may be used to treat a variety of types of pain. PNFS may be particularly effective at treating localized types of pain. For example, PNFS may be used to treat pain associated with failed back surgery syndrome (FBBS) or other low back pain, cervical pain, such as in the shoulder or neck, neuralgia or other pain associated with occipital nerves, supra-orbital pain, facial pain, inguinal or other pelvic pain, intercostal or other chest pain, limb pains, phantom limb pain, visceral pain, especially if it is referred to a superficial structure, peroneal pain, or arthritis.

PNFS may ameliorate pain within the region through stimulation of axons or small nerve fibers in the nearby dermal, subcutaneous, or muscular tissues, or the dermal, subcutaneous, or muscular tissues themselves. The stimulation may cause orthodromic action potentials that propagate toward the spinal cord, and modulate larger peripheral nerves and dorsal horn cells and/or synapses within the dermatomes that include the pain region, which may reduce pain experienced by a patient in that region. The patient may experience paresthesia in the dermatome where the electrodes are placed. The stimulation of these axons or fibers may also cause antidromic action potentials that propagate toward the skin and modulate sympathetic outflow, which may reduce pain mediated by the sympathetic system, such as is the case with some forms of complex regional pain syndrome. The electrodes that deliver PNFS are not implanted proximate to or aligned with larger, peripheral nerves, to avoid delivery of stimulation to smaller fibers in the peripheral nerves, e.g., A-delta fibers, which may result in a patient experiencing unpleasant sensations.

By way of contrast, peripheral nerve stimulation (PNS) involves delivery of stimulation to a specific peripheral nerve via one or more electrodes implanted proximate to or in contact with a peripheral nerve, e.g., cuff electrodes surrounding the peripheral nerve. PNS may be used to deliver stimulation to, for example, the vagal nerves, cranial nerves, trigeminal nerves, ulnar nerves, median nerves, radial nerves, tibial nerves, and the common peroneal nerves. When PNS is delivered to treat pain, one or more electrodes are implanted proximate to or in contact with a specific peripheral nerve that is responsible for the pain sensation.

PNS causes orthodromic action potentials to propagate to the spinal cord via the specific peripheral nerve, diminishing pain. Typically, however, the peripheral nerve, and thus the electrodes implanted proximate to the peripheral nerve, are located "upstream" from the region in which a patient perceives the pain, i.e., closer to the spinal cord than the region of pain. For PNS therapy, it is considered desirable to implant the electrodes upstream from the region in which a patient perceives pain so that the paresthesia resulting from PNS is as widely distributed as the areas innervated by the peripheral nerve.

Delivery of PNFS by an IMD according to the invention may occur in combination with one or more other types of therapy, such as delivery of spinal cord stimulation (SCS). A combination therapy that includes PNFS and one or more other types of therapy may be able to more completely address complex and/or multifocal pain than would be possible through delivery of either PNFS or the other therapies alone. Further, combining PNFS with one or more other types of therapy may reduce the likelihood that neural accommodation will impair the perceived effectiveness of any of the therapies.

As another example, the other therapy delivered in combination with PNFS may be a drug. In such embodiments, another IMD may include a reservoir and pump to deliver the drug. The other therapy delivered in combination with PNFS, whether electrical stimulation, a drug, or some other therapy, need not be delivered by the same IMD as that which delivers PNFS, as mentioned above, or an IMD at all. For example, the other therapy may be delivered by an external medical device, or a non-device delivery modality, such as ingestion of a drug. SCS, PNS, deep brain stimulation (DBS), cortical stimulation, and one or more drugs are examples of other therapies that may be delivered in combination with PNFS.

PNFS and the one or more other therapies may be delivered simultaneously, or in an interleaved or alternating fashion. For example, one or more IMDs may deliver PNFS and an additional therapy, e.g., DBS or SCS, in an alternating or interleaved fashion, e.g., each pulse delivered according to different one of the therapies. As another example, the different neurostimulation therapies may have different pulse rates, duty cycles or scheduled times for delivery, which may result in alternating delivery of the therapies. Interleaved or alternating delivery of PNFS and one or more other therapies may, for example, reduce the likelihood that neural accommodation or tolerance to a particular drug will impair the efficacy of one or more of the therapies, while still providing therapy at any given time. Further, any or all of the combined therapies may be delivered selectively, e.g., upon request by a user, such as a patient or physician.

In one embodiment, the invention is directed to an implantable medical device comprising a housing that includes a first surface and a second surface, a plurality of electrodes, wherein a first set of the electrodes is located on a first surface of the housing, and a second set of the electrodes is located on a second surface of the housing, and a stimulation generator within the housing configured to deliver electrical stimulation to a patient via the first and second sets of the electrodes.

In another embodiment, the invention is directed to a method comprising selecting from among a plurality of electrodes on a housing of an implantable medical device, wherein the housing includes a first surface and a second surface, a first set of the electrodes are located on the first surface, and a second set of the electrodes is located on the second surface, and delivering electrical stimulation from the implantable medical device to a patient via the selected electrodes.

In another embodiment, the invention is directed to a method comprising forming a housing for an implantable medical device, the housing including a first surface and a second surface, forming a first set of one or more electrodes on the first surface of the housing, forming a second set of one or more electrodes on the second surface of the housing, and coupling a stimulation generator to the first and second sets of electrodes The invention may provide advantages. For example, the IMD may be relatively small and thin, which may facilitate implantation within any of the target tissue layers discussed above, and within any of a variety of regions of the body of a patient. The IMD may include multiple electrodes on two or more surfaces of the IMD housing to reduce the need for tunneling leads to target tissues of the patient. Further, location of electrodes on multiple surfaces of the housing may allow the IMD to deliver stimulation to a variety of tissues proximate to the IMD, and with a variety of current field configurations. Additionally, distribution of electrodes over substantially the entire surface may provide flexibility in selecting electrodes, and thereby provide flexibility in selecting a location, size and shape of a current field resulting from delivery of stimulation by the IMD via the selected electrodes.

As an example, the size of the IMD may facilitate implantation within a region in which the patient experiences pain for delivery of PNFS. The region in which the patient experiences pain may also be described as the region where the patient perceives the pain to be located. Further, the size of IMD may facilitate implantation within or between one or more of the intra-dermal, deep dermal, or subcutaneous tissue layers of the region. With electrodes located on multiple surfaces of the IMD, a clinician may select combinations of the electrodes such that the current field resulting from delivery of PNFS by the IMD stimulates tissues within one or more of the layers. The ability to selectively stimulate tissue in one or more of the layers provided by an IMD with electrodes located on multiple surfaces of its housing may allow the clinician to better identify an electrode combination that provides desirable stimulation in terms of efficacy, e.g., amelioration of pain, and side effects. The number of electrodes and extent to which they are spatially distributed over substantially all of the two or more housing surfaces may increase the flexibility in stimulation programming from the perspective of the clinician.

Embodiments in which the IMD, either alone or in cooperation with one or more other IMDs or therapy delivery modalities, delivers PNFS in combination with other types of therapy may be able to more completely address complex or multifocal pain than would be possible through delivery of either PNFS or the other therapies alone. For example, pain areas often involve a substantial portion of one limb, and involve more than one dermatome. SCS is often used in this case. SCS may provide paresthesia to the lower back, an entire limb, and/or portions of more than one limb. If a patient also has a focal site of pain (axial back, ribs, prior site of surgery, one knee), SCS may not ameliorate the pain, particularly if it is nociceptive pain. In such cases, PNFS may be delivered to the site of the focal pain in combination with SCS or a different therapy to more completely address the pain experienced by the patient. In other words, an IMD according to the invention may allow the patient relief from pain that is not readily treated by other pain management techniques alone.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
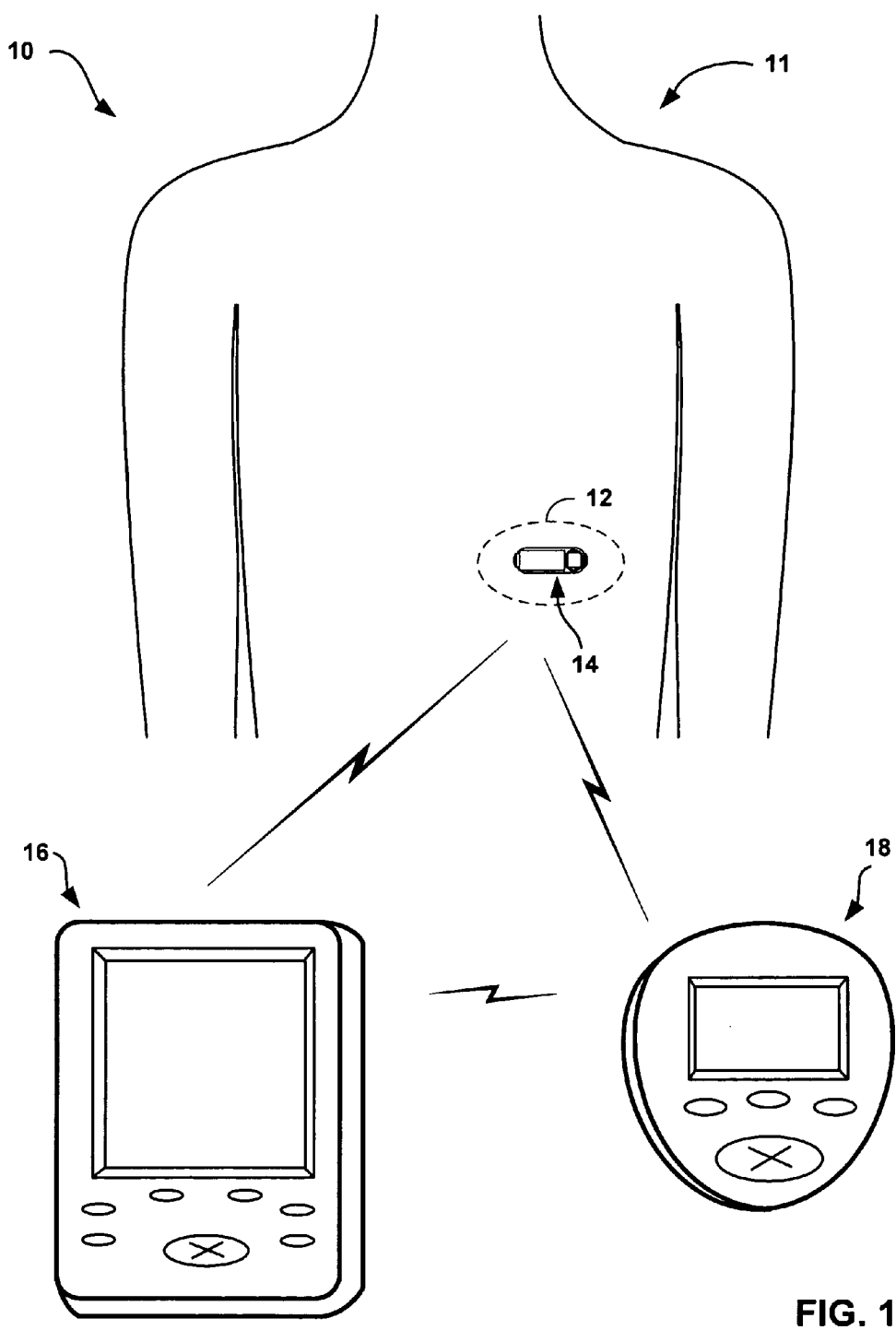
FIG. 1 is a conceptual diagram illustrating an example system that includes an implantable medical device with electrodes on multiple housing surfaces.

FIG. 1 is a conceptual diagram illustrating an example system 10 that includes an IMD 14. As will be described in greater detail below, IMD 14 includes a housing (not shown in FIG. 1) that contains internal components, such as control electronics, stimulation generation circuitry, communication circuitry, and a power source. IMD 14 also includes electrodes (not shown in FIG. 1) located on at least two of the surfaces of the housing. IMD 14 delivers electrical stimulation via combinations of the electrodes, which may include electrodes from one or more of the housing surfaces. In some embodiments, the stimulation generation circuitry within IMD 14 is pulse generation circuitry, and IMD 14 delivers stimulation in the form of electrical pulses.

IMD 14 may have miniaturized form factor and a low profile that permits implantation within inter-dermal, deep dermal, or subcutaneous tissue of patient 11. For example, IMD 14 may be implanted under a flap of skin. These tissues include skin and associated nerves and muscles and associated nerves or muscle fibers. IMD 14 may be generally thin and flat and, in some embodiments, may be angled or curved to better conform to the tissues at location where the IMD is implanted. In this manner, IMD 14 may exhibit a low profile such that it may be barely noticeable to patient 11 and others when implanted within the patient. IMD 14 may be chronically or temporarily implanted within patient 11.

In the example illustrated by FIG. 1, IMD 14 is implanted within a region 12 in which a patient 11 experiences pain. IMD 14 may, for example, deliver peripheral nerve field stimulation (PNFS) to inter-dermal, deep dermal, and/or subcutaneous tissues within region 12 to ameliorate the pain experienced by patient 11. In the illustrated example, region 12 is an axial region of the lower back of patient 12, but the invention is not limited as such. Rather, IMD 14 may be implanted in any region, localized area or dermatome where patient 11 experiences pain. As examples, IMD 14 may be implanted within various regions of the back, the back of the head, above the eyebrow, over the eye, or under the eye. IMD 14 may deliver PNFS to, for example, treat failed back surgery syndrome (FBBS), cervical pain (shoulder and neck pain), facial pain, headaches supra-orbital pain, inguinal and pelvic pain, chest and intercostal pain, mixed pain (nociceptive and neuropathic), visceral pain, neuralgia, peroneal pain, phantom limb pain, and arthritis.

PNFS may ameliorate pain within the region of implantation by stimulating axons or small nerve fibers in the nearby dermal, subcutaneous, or muscular tissues, or the tissues themselves. The stimulation of these axons or fibers may cause orthodromic action potentials that propagate toward the spinal cord of patient 11, and modulate larger peripheral nerves and dorsal horn cells and/or synapses within the dermatomes that include the pain region, which may reduce pain experienced by patient 11 in that region. The stimulation of these axons or fibers may also cause antidromic action potentials that propagate toward the skin and modulate sympathetic outflow, which may reduce pain mediated by the sympathetic system, such as with some forms of complex regional pain syndrome. IMD 14 is not implanted proximate to larger, peripheral nerves in order to avoid delivery of stimulation to smaller fibers in the nerve, e.g., A-delta fibers, which may result in a patient experiencing unpleasant sensations.

In the illustrated embodiment, system 10 includes only a single IMD 14 to deliver PNFS. However, embodiments may include one or more IMDs 14 for delivery of PNFS to one or more pain regions. Further, PNFS may be delivered alone, or in combination with other therapies as will be described below.

Moreover, although described herein primarily with reference to PNFS, the invention is not limited to embodiments in which one or more IMDs deliver PNFS. IMDs with electrodes located on multiple housing surfaces according to the invention may be implanted within any region of the body, to provide any of a variety of therapies. For example, an IMD with electrodes located on multiple housing surfaces may be implanted within the limbs to, for example, provide functional electrical stimulation. As another example, an IMD with electrodes located on multiple housing surfaces may be implanted within or proximate to the gastrointestinal tract and deliver electrical stimulation to, for example, treat gastroparises or other gastric motility disorders. As yet another example, an IMD with electrodes located on multiple housing surfaces may be implanted within or proximate to the sacral nerves or pelvic floor and deliver electrical stimulation to, for example, treat incontinence or sexual dysfunction.

As illustrated in FIG. 1, system 10 may include external programmers 16 and 18, which may respectively be used by a clinician and patient 11 to communicate with IMD 14, e.g., via wireless telemetry. As illustrated in FIG. 1, programmers 16 and 18 may also communicate with each other. The clinician may use programmer 16 to program the stimulation delivered by IMD 14. For example, the clinician may test a number of stimulation programs by controlling IMD 14 to deliver stimulation according to the programs and observing the results of the stimulation, e.g., receiving feedback from the patient as to the efficacy and side effects of delivery of stimulation according to the program.

Each program may include a plurality of stimulation parameters. For example, in embodiments in which IMD 14 delivers stimulation in the form of pulses, the parameters for each program may include a voltage or current pulse amplitude, a pulse width, and a pulse rate. The parameters may also include an electrode configuration, which refers to the combination of electrodes used for delivery of stimulation, and their polarities. The combination of electrodes for each program may include electrodes located on one or more of the surfaces of the housing of IMD 14. In other words, each program may specify delivery of stimulation via electrodes on a single housing surface, or specify delivery of stimulation between electrodes located on multiple surfaces. In some embodiments, cathode and anode electrode pairs may be located on separate surfaces of IMD 14. In this manner, electrical current may travel along a side surface of IMD 14.

In other embodiments, parameters may differ between electrodes on one surface of IMD 14 and electrodes on another surface of the IMD. For example, electrodes on separate surfaces of IMD 14 may deliver pulses with different pulse widths. Differences in current amplitude, voltage amplitude, pulse frequency, or other parameters may also be possible with IMD 14.

The location of electrodes on multiple surfaces of the housing of IMD 14 may provide flexibility to the clinician in selecting electrodes, and thereby provide flexibility in selecting a location, size and shape of a current field resulting from delivery of stimulation by the IMD via the selected electrodes. With electrodes located on multiple surfaces of IMD 14, a clinician may select combinations of the electrodes such that the current field resulting from delivery of stimulation by IMD 14 stimulates tissues within one of the layers, or within multiple layers. The ability to selectively stimulate tissue in one or more of the layers may allow the clinician to better identify an electrode combination that provides desirable stimulation in terms of efficacy, e.g., reduction of pain, and side effects.

Based on their efficacy and side effects, the clinician may select one or more of the tested programs. Clinician programmer 16 may then provide the selected programs to IMD 14 or patient programmer 18 for longer-term storage and use by patient 11. Patient 11 may use patient programmer 18 to, for example, select one or more programs from among the stored programs to control delivery of therapy by IMD 14, make adjustments to the programs, or start and stop delivery of stimulation.

IMD 14, clinician programmer 16 and patient programmer 18 may, as shown in FIG. 1, communicate via wireless communication. Clinician programmer 16 and patient programmer 18 may, for example, communicate via wireless communication with IMD 14 using any telemetry techniques known in the art. Such techniques may include low frequency or radiofrequency (RF) telemetry, but other techniques are also contemplated. Clinician programmer 16 and patient programmer 18 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 16 and patient programmer 18 need not communicate wirelessly, however. For example, programmers 16 and 18 may communicate via a wired connection, such as via a serial communication cable, or via exchange of removable media, such as magnetic or optical disks, or memory cards or sticks. Further, clinician programmer 16 may communicate with one or both of IMD 14 and patient programmer 18 via remote telemetry techniques known in the art, communicating via a local area network (LAN), wide area network (WAN), public switched telephone network (PSTN), or cellular telephone network, for example.

Figure 2A:
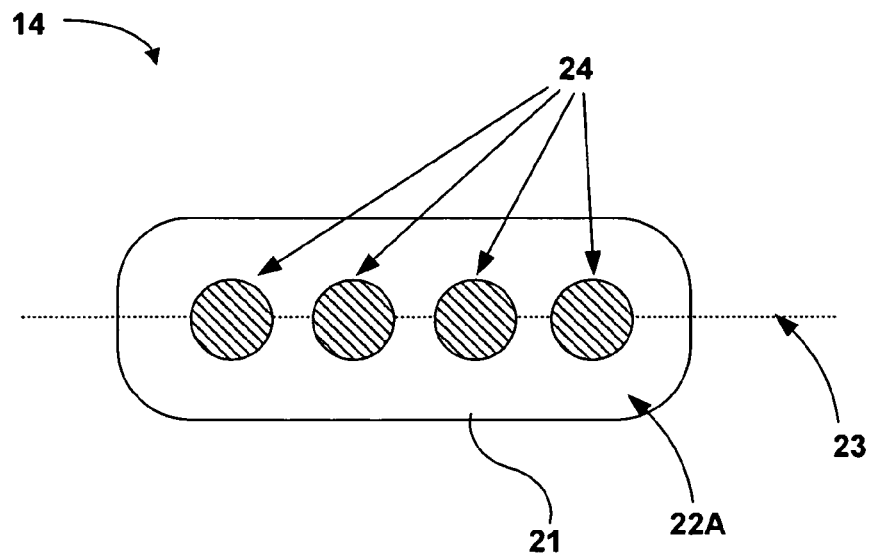
FIGS. 2A and 2B are schematic diagrams respectively illustrating top and side views of the implantable medical device of FIG. 1 with electrodes located on a top surface and a bottom surface of the implantable medical device housing.
Figure 2B:
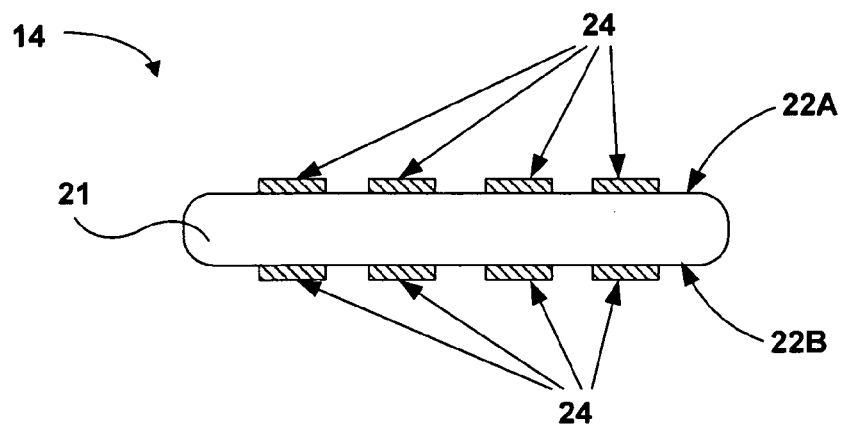

FIGS. 2A and 2B are schematic diagrams respectively illustrating top and side views of IMD 14. As illustrated in FIGS. 2A and 2B, IMD 14 includes a housing 21 with a top surface 22A and a bottom surface 22B. IMD 14 also includes a plurality of electrodes 24. A first subset of electrodes 24 is located on top surface 22A, while a second subset of electrodes 24 is located on bottom surface 22B.

IMD 14 may deliver electrical stimulation, e.g., pulses, via a selected combination of electrodes 24 from one or both of top surface 22A and bottom surface 22B. When IMD is implanted within or between one or more of the inter-dermal, deep dermal, and/or subcutaneous tissue layers, the subsets of electrodes 24 on the housing surfaces 22 may be respectively located more proximate to different ones of the layers. The ability of a clinician to select electrodes 24 from one or both of housing surfaces 22 for an electrode configuration for a stimulation program, may allow the clinician to select a current field configuration that stimulates a desired one or more of the tissue layers. In other words, an IMD 14 with electrodes 24 located on multiple housing surfaces 22 according to the invention may selectively stimulate any one or more tissue layers.

As illustrated in FIG. 2B, top and bottom housing surfaces 22A and 22B (collectively "housing surfaces 22") may be substantially parallel, opposing, major surfaces of housing 21. A "major" surface of a housing has a relatively large surface area when compared to other surfaces. For example, top and bottom housing surfaces 22 are major surface in that they have a relatively large surface area when compared to the side surfaces of housing 21. While electrodes 24 are shown located on opposing, substantially parallel surfaces 22 of housing 21, electrodes 24 may be located on adjacent surfaces of the housing, e.g., top surface 22A and one of the side surfaces of housing 21. In some alternative embodiments, electrodes 24 may be located on three or more surfaces of housing 21.

In the example illustrated by FIG. 2A, electrodes 24 are distributed over substantially the entire length of top surface 22A. Further, electrodes 24 are arranged in a row substantially along an axis 23 of top surface 23. However, the invention is not limited to the illustrated arrangement of electrodes 24, or any particular arrangement of electrodes. For example, electrodes may be arranged on surfaces in multiple rows substantially parallel to axis 23, in a substantially "checkerboard-like" pattern, or a substantially irregular pattern. Further, electrodes 24 may be distributed across substantially the entirety of one or both of surfaces 22, or may be grouped into one or more discrete clusters at various positions on the surface.

Moreover, the number, size and shape of electrodes 24 illustrated in FIGS. 2A and 2B are merely exemplary. IMD 14 may include as few as a single electrode 24 on each of housing surfaces 22. Further, although illustrated as substantially flat electrode pads with substantially circular cross-sectional shapes, electrodes 24 may have any two or three-dimensional shape. In alternative embodiments, electrodes 24 may be located on adjacent surfaces of IMD 14, such as a side of the housing. These electrodes may be in addition to or in place of electrodes 24 on housing surfaces 22. In other embodiments, electrodes may be located on an edge of IMD 14.

Figure 3A:
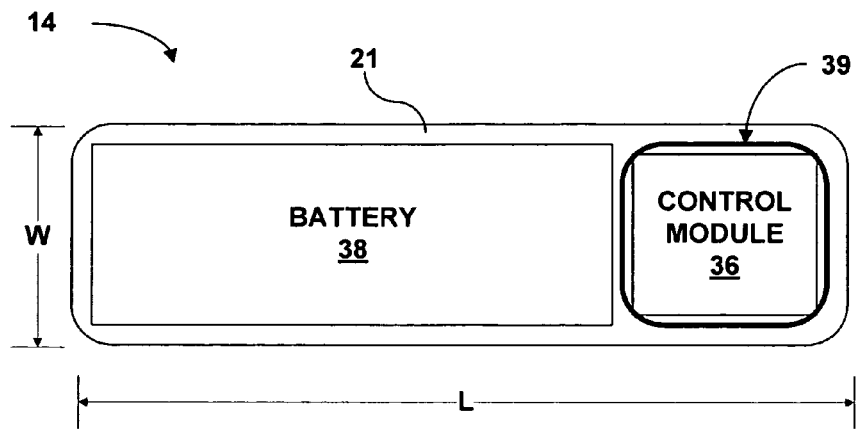
FIGS. 3A and 3B are schematic diagrams respectively illustrating top and side cross-sectional views of the implantable medical device of FIG. 1.
Figure 3B:
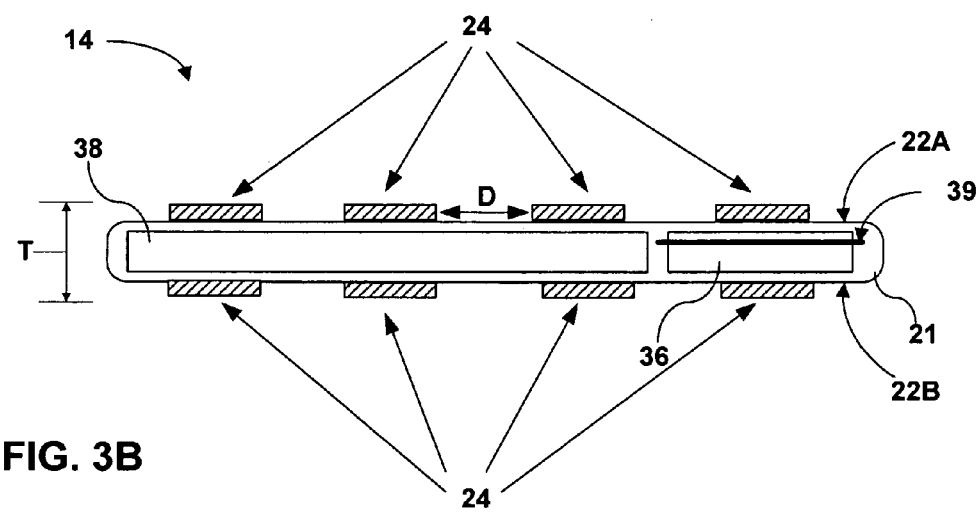

FIGS. 3A and 3B are schematic diagrams respectively illustrating top and side cross-sectional views of IMD 14. As shown in FIGS. 3A and 3B, housing 21 of IMD 14 houses a control module 36, a battery 38, and a coil 39 encircling control module 36. In some embodiments, coil 39 may encircle control module 36, battery 38, or both.

Control module 36 receives power from battery 38 to drive the electrodes 24 according to one or more stimulation programs, which may be stored within control module 36 and/or received from one of programmers 16, 18, e.g., via radio frequency (RF) or inductive telemetry. Control module 36 may include control electronics, such as any one or more of a microprocessor, digital signal processor (DSP), application-specific integrated circuit (ASIC), field-programmable gate array (FPGA), or other digital logic circuitry. Control module 36 may also include memory, such as any one or more of read-only memory (ROM), random-access memory (RAM), non-volatile RAM (NVRAM), electronically-erasable programmable ROM (EEPROM), or flash memory. The memory of control module may store stimulation programs, as well as program instructions that, when executed by the control circuitry of control module 36, cause control module 36 and IMD to provide the functionality ascribed to them herein. Control module 36 may also include stimulation generation circuitry, such as voltage or current pulse generators that include capacitors, regulators, current mirrors, or the like, as is known in the art.

Battery 38 may be rechargeable, and may have a capacity of at least 20 milliamp-hr, more preferably at least 25 milliamp-hr, and still more preferably at least 30 milliamp-hours. In this case, battery 38 comprises a capacity almost an order of magnitude larger than conventional microstimulators. In some embodiments, battery 38 may comprise a lithium ion rechargeable battery.

Coil 39 may serve as a telemetry coil for wireless communication with an external programmer, e.g., programmers 16 and 18. Coil 39 may be formed of windings of copper or another highly conductive material. In some embodiments in which battery 38 is rechargeable, coil 39 may also act as an inductive power interface to recharge battery 38, e.g., may inductively receive energy from an external recharging unit (not illustrated) through the skin of patient 11 to recharge battery 38. In other embodiments, separate coils may be provided for communication and recharging.

Further, the invention is not limited to embodiments in which battery 38 is rechargeable, or in which IMD 14 includes a battery. For example, IMD 14 may include a non-battery power source, such as a supercapacitor. In other embodiments, IMD 14 may not store power, and control module 36 may instead receive power substantially continuously from an external source via coil 39 or another coil.

Housing 21 may be formed from any of a variety of materials such as silicone, polyurethane, other polymeric materials, titanium, stainless steel or ceramics. As shown in FIG. 3A, housing 21 conforms to a substantially rectangular form factor. In alternative embodiments, housing 21 may include curved, angled, or asymmetric edges such that the housing fits within the implant region of the patient. Housing 21 may conform to a miniaturized form factor with a low profile in order to fit within a desired layer of tissue for implant.

IMD 14 or housing 21 may have a length (L) of approximately 30 to 120 mm, a width (W) of approximately 10 to 25 mm and a thickness (T) of approximately 3 to 8 mm. In some embodiments, IMD 14 or housing 21 may have a length (L) less than approximately 50 mm, and a thickness (T) of less than approximately 6 mm. In some embodiments, IMD 14 or housing 21 comprises a length (L) of less than or equal to 36.6 mm (1.44 inches), a width (W) of less than or equal to 14.5 mm (0.57 inches), and a thickness (T) of less than or equal to 4.5 mm (0.177 inches). In some embodiments, IMD 14 may include approximately 0.25 mm (0.01 inches) of insulation between control module 36, battery 38 and housing 21. The walls of housing 21 may comprise a total thickness of approximately 0.71 mm (0.03 inches).

Control module 36 and coil 39 are designed to be very thin and flat to fit within housing 21. For example, control module 36 may comprise a length of less than or equal to approximately 6.5 mm (0.256 inches), a width of less than or equal to approximately 9.4 mm (0.37 inches), and a thickness of less than or equal to approximately 3.6 mm (0.14 inches). Further, although battery 38 comprises a capacity almost an order of magnitude larger than some conventional microstimulators, battery 38 has a relatively small capacity compared to full size IMDs. Therefore, coil 39 may be smaller than coils within traditional IMDs. Coil 39 may comprise inner dimensions slightly larger than the dimensions of control module 36 given above.

Coil 39 may comprise an inner length of approximately 6.7 mm (0.265 inches) and an inner width of approximately 9.7 mm (0.38 inches). The outer dimensions of coil 39 may comprise an outer length of approximately 8.4 mm (0.33 inches) and an outer width of approximately 11.7 mm (0.46 inches). Coil 39 may also comprise a thickness of approximately 2.5 mm (0.10 inches).

Similarly, battery 38 may be configured to fit within the relatively thin and flat housing 21. For example, battery 38 may be a lithium ion battery with a thin, generally flat housing or cylindrical housing. In the case of a pin type cell, battery 38 may have an aluminum housing with a crimped or riveted pin feedthrough. In some embodiments, battery 38 alternatively may comprise a foil pack battery.

Battery 38 may comprise a length of less than or equal to approximately 24.9 mm (0.98 inches), a width of less than or equal to approximately 12.7 mm (0.50 inches), and a thickness of less than or equal to approximately 3.3 mm (0.13 inches). Battery 38 may be loaded with electrical charge in a standard or adjustable manner, which may affect the dimensions of possible battery dimensions. Battery 38 may conform to one of a variety of designs. Some examples are given in Table 1 below.

TABLE 1

|  | 3.0 mm thick standard loading | 3.0 mm thick adjustable loading | 3.3 mm thick standard loading | 3.3 mm thick adjustable loading |
| --- | --- | --- | --- | --- |
| Length (mm) | 25.4 | 25.4 | 25.4 | 24.9 |
| Width (mm) | 16.5 | 14.2 | 13.2 | 12.7 |
| Capacity (mA-hr) | 30 | 30 | 31 | 30 |
| Battery Case Volume (cc) | 1.26 | 1.08 | 1.11 | 1.04 |
| Coating Deposition (mg/cm$^2$) | 22 | 12.1 | 22 | 12.32 |

IMD 14 may be over-discharge protected. However, since battery 38 conforms to an extremely small form factor, the over-discharge protection may be difficult to realize using traditional approaches, such as extra battery capacity. Therefore, IMD 14 may include a switch to disconnect battery 38 from the load, e.g., an adjustable loading battery, when a predetermined voltage is reached. In other cases, battery 38 may comprise an over-discharge tolerant battery.

Each of electrodes 24 may be substantially circular, square or rectangular, or may have other cross-sectional shapes or substantially irregular cross-sectional shapes. In the case of a circular cross-sectional shape, each electrode 24 may have a diameter of approximately 0.5 mm to 1.5 mm, and more preferably 1 mm. IMD 14 may include between 2 and 32 electrodes, although greater numbers of electrodes are possible. Inter-electrode distances (D) on surfaces 22 may be within a range from approximately 0.1 mm to approximately 5.0 mm, and in some embodiments may be approximately to 0.5 mm.

Electrodes 24 may be distributed on each of housing surfaces 22 in a linear or a two-dimensional array. A linear array generally refers to an ordering of electrodes 24 along a common line or axis, such as axis 23 illustrated in FIG. 2A, whereas a two-dimensional array generally refers to an ordering of electrodes 24 along at least two different lines, e.g., as rows and columns, or a checkerboard pattern. In either case, the array of electrodes 24 may have a regular, periodic pattern such that electrodes are positioned at regular spatial intervals within a line, row or column.

Alternatively, the array may be irregular such that electrodes 24 are positioned at irregular intervals or at positions that do not represent an ordered pattern. Further, as discussed above, electrodes 24 need not be located substantially along substantially the entire lengths or across substantially the entire surface areas of housing surfaces 22. Instead, electrodes 24 may be clustered or grouped at particular locations on the surfaces. However, distributing electrodes 24 along substantially the entire length or across substantially the entire surface area of a housing surface 22 may enable IMD 14 to selectively stimulate tissues within a larger region, which may make it more likely that a desirable electrode configuration and stimulation program in terms of efficacy and side effects will be discovered.

Figure 4A:
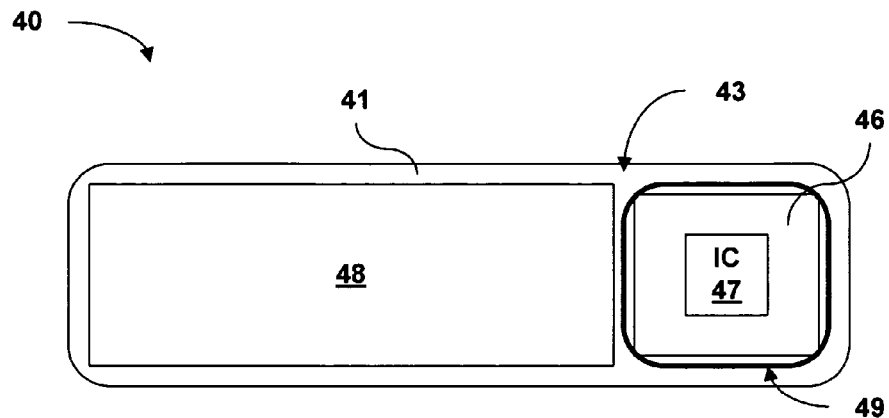
FIGS. 4A and 4B are schematic diagrams respectively illustrating top and side cross-sectional views of another example implantable medical device with electrodes located on multiple housing surfaces, in which the housing includes a bend.
Figure 4B:
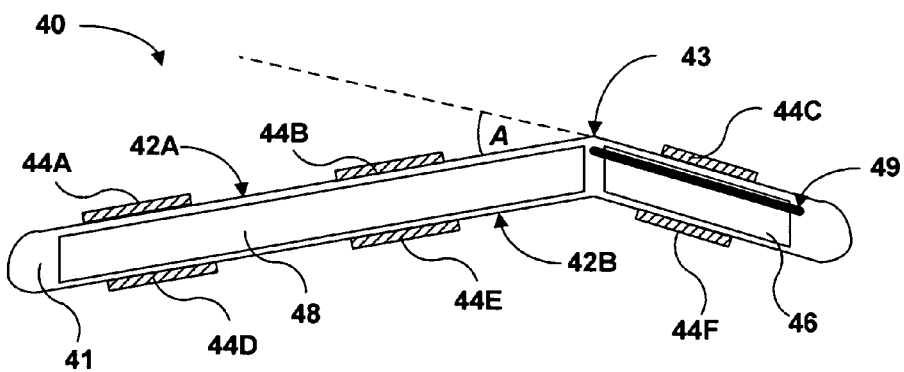

FIGS. 4A and 4B are schematic diagrams respectively illustrating top and side cross-sectional views of another example IMD 40. IMD 40 includes a housing 41 with a top surface 42A and a bottom surface 42B, and electrodes 44A-C and 44D-F located on top surface 42A and bottom surface 42B, respectively. Electrodes 44A-F (collectively "electrodes 44") may be substantially similar to electrodes 24 discussed above, and arranged on surfaces 42A and 42B (collectively "housing surfaces 42") in substantially the same manner as discussed above with reference to electrodes 24.

Like housing 21 of IMD 14, housing 41 contains a control module 46 which provides substantially the same functionality as discussed above with reference to control module 36 of IMD 14 and FIGS. 3A and 3B. Housing 41 also contains battery 48 and coil 49 substantially similar to battery 38 and coil 39 discussed above with reference to IMD 14. In general, housing 41 may be substantially in most respects housing 21 described above with reference to IMD 14 and FIGS. 3A and 3B.

However, as illustrated in FIG. 4B, housing 41 may also comprise a degree of curvature, or angle, to conform to tissues at an implantation site for IMD 40. Housing 41 may be formed with the angle or degree of curvature. In other cases, a clinician may bend housing 41 to a degree of curvature appropriate for a specific stimulation site. For example, housing 41 may comprise a flexible material or include bellows that allow housing 41 to bend. In other embodiments, housing 41 may include a hinge that may rotate to allow the housing to change its curvature. The hinge may include a screw or other limiting mechanism to set the hinge to a desired degree of curvature.

In the example of FIGS. 4A and 4B, housing 41 is defines an angle (A) at a boundary 43 between a portion of the housing containing control module 46 and a portion containing battery 48. The angle (A) may be approximately 10 to 45 degrees, and more preferably approximately 30 degrees. Boundary 43 is illustrated in FIG. 4B as defining a sharp transition, but include a rounded curvature in other embodiments. Further, although a single boundary and angle are illustrated, IMDs according to the invention may include multiple boundaries and angles.

As illustrated in FIG. 4A, control module 46 comprises an application specific integrated circuit, e.g., IC 47, designed to minimize the number of components within IMD 40. IC 47 may be designed using the 0.8 micron process in an effort to reduce the overall size and profile of IMD 40. With sufficient processing power, IC 47 may have a footprint of approximately 5.2 mm (0.204 inches) by 5.2 mm and a thickness of approximately 0.46 mm (0.018 inches).

IC 47 may be application specific to minimize the components needed by the IC for operation. The ASIC may include both a battery recharge module and a telemetry module that couple to coil 49, as well as a pulse generator and processor. The processor directs the pulse generator to drive one or more electrodes based on stimulation programs stored in memory accessible by the control module 46 or received by the telemetry module. A power management module coupled to battery 48 powers the control circuitry and pulse generator within control module 46.

Figure 5:
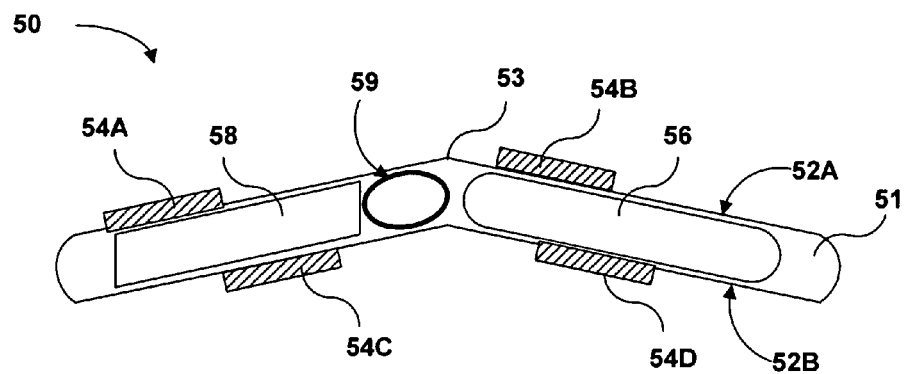
FIG. 5 is a schematic diagram illustrating a side cross-section view of another example implantable medical device with electrodes located on multiple housing surfaces and in which the housing includes a bend.

FIG. 5 is a schematic diagram illustrating a side cross-sectional view of another example IMD 50. IMD 50 includes a housing 51 with a top surface 52A and a bottom surface 52B, electrodes 54A and 54B located on top surface 52A, and electrodes 54C and 54D located on bottom surface 52B. Electrodes 52A-D (collectively "electrodes 52") may be substantially similar to electrodes 24 discussed above, and arranged on surfaces 52A and 52B (collectively "housing surfaces 52") in substantially the same manner as discussed above with reference to electrodes 24. Further, IMD 50 includes a control module 56, battery 58 and coil 59 within housing 51, which may be substantially similar to and provide substantially the same functionality as any of the control modules, batteries and coils discussed above. Additionally, like housing 41 discussed above with reference to FIGS. 4A and 5B, housing 51 defines an angle at a boundary 53, which may be substantially similar to angle (A) discussed above with reference to housing 41.

However, unlike coils 39 and 49 of IMDs 14 and 40, coil 59 of IMD 50 does not substantially surround control module 56. Instead, coil 59 is located between battery 58 and control module 56, proximate to the boundary at which housing 51 is angled. Again, in various embodiments, a coil may substantially surround a control module, battery, both the control module and the battery, or, as illustrated in FIG. 5, neither the control module nor the battery.

Figure 6:
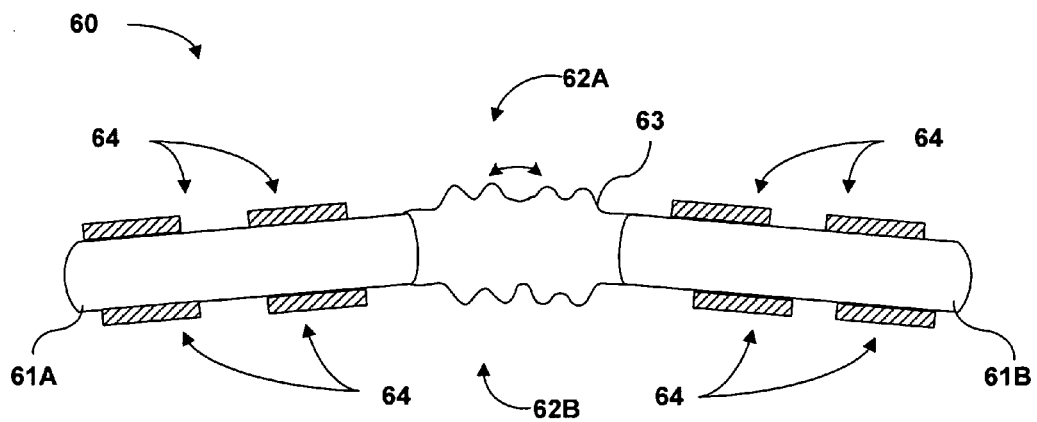
FIG. 6 is a schematic diagram illustrating a side cross-section view of another example implantable medical device with electrodes located on multiple housing surfaces, in which the housing includes a bellows that allows the housing to conform to an implant site.

FIG. 6 is a schematic diagram illustrating a side view of another example IMD 60. IMD 60 includes a housing with two housing portions 61A and 61B, a top surface 62A, bottom surface 62B, and electrodes 64 located on the top and bottom surfaces. Although not illustrated in FIG. 6, IMD 60 may include a control module, battery and coil, substantially similar those discussed above, distributed through the housing section 61A and 61B.

First and second housing sections 61A and 61B may be formed from a variety of materials such as titanium, stainless steel, ceramic material, silicone, polyurethane or other polymeric materials. Since IMD 60 will be in contact with bodily fluids and tissues, each exposed material should be resistant to corrosion, e.g., bio-compatible. First and second housing sections 61A and 61B may conform to a substantially miniaturized form factor and a small diameter to fit within the stimulation site.

First and second housing sections 61A and 61B are connected by a bellows-like joint 63 that allows bending of IMD 60. FIG. 6 illustrates IMD 60 in a slightly bent position to better conform to an implantation site. For example, the physician may bend IMD 60 about bellows-like joint 63 to a degree of curvature that conforms to a radius of the specific stimulation site and tissue area.

Bellows-like joint 63 may comprise titanium, nitinol, or another biocompatible material resistant to fatigue and strong enough to accommodate flexing without damage. In alternative embodiments, bellows-like joint 63 may be constructed of a polymer such as polypropylene, polyurethane, or polyethylene. Bellows-like joint 63 may be substantially smaller relative to IMD 60 if the material of bellows-like joint 63 is able to withstand the increased flexing force.

Figure 7A:
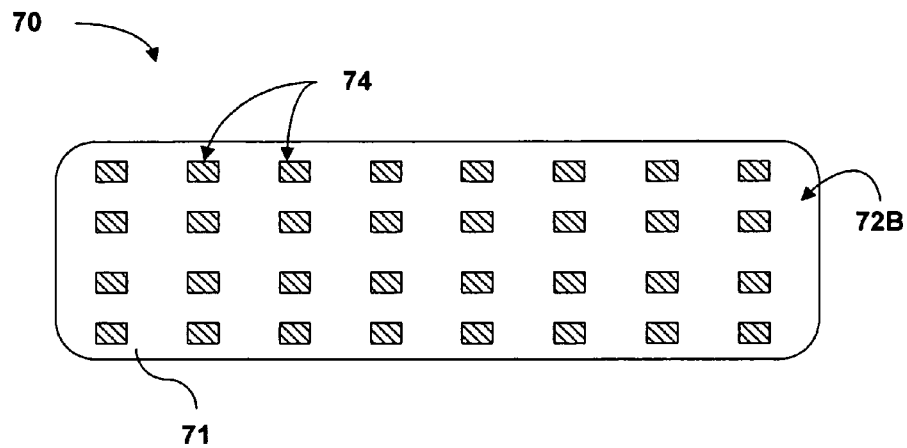
FIGS. 7A and 7B are schematic diagrams respectively illustrating a bottom view and a side cross-sectional view of another example implantable medical device with electrodes located on multiple housing surfaces, in which the top and bottom housing surfaces are respectively convex and concave.
Figure 7B:
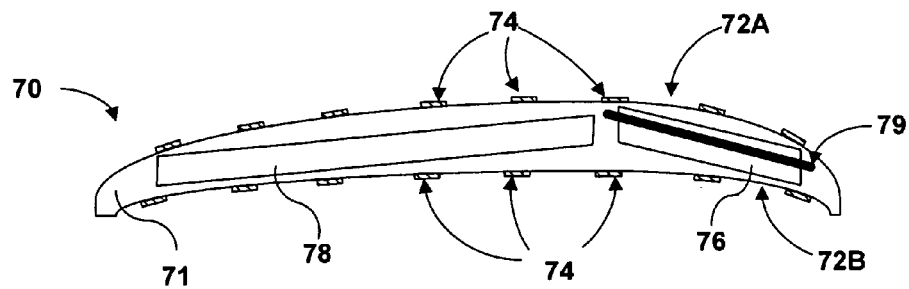

FIGS. 7A and 7B are schematic diagrams illustrating a bottom view and side cross-sectional view, respectively, of another example IMD 70. IMD 70 comprises a housing 71 with a top surface 72A and a bottom surface 72B, each of which includes a two-dimensional array of electrodes 74. As illustrated in FIG. 7A, the two-dimensional arrays of electrodes may cover substantially the entire surface areas of housing surfaces 72A and 72B.

Similar to the other embodiments described above, IMD 70 includes a control module 76, battery 78 and coil 79 within housing 71. Each of electrodes 74 may be coupled to control module 76. Control module 78 may include stimulation generation circuitry to deliver stimulation according to a stimulation program via a combination of electrodes 76 specified by the program. The combination of electrodes may be, for example, a bipolar pair of electrodes on one or both of housing surfaces 72A and 72B.

Control module 76 within IMD 70 can be programmed to apply stimulation via selected combinations of electrodes 74 to achieve desired efficacy. In particular, at the time of implantation, a clinician may test different programs and their associated electrode combinations, and then program IMD 70 with one of more of tested programs. As mentioned previously, programming of IMD 70 may take place through communication of control module 66 with programmers 16, 18 by wireless telemetry via coil 79.

As discussed above, an IMD housing may define an angle between portions of the housing, thereby promoting conformance to the stimulation site. In other embodiments, a housing may have a general curvature instead of localized angle to promote conformance to the stimulation site. For example, top surface 72A and bottom surface 72B of housing 71 illustrated in FIG. 7B respectively are convex and concave. The curvature of the surfaces 72A and 72B of housing 71 may have a radius between 10 centimeters (cm) and 100 cm, according to the dimensions of the implant site.

Figure 8:
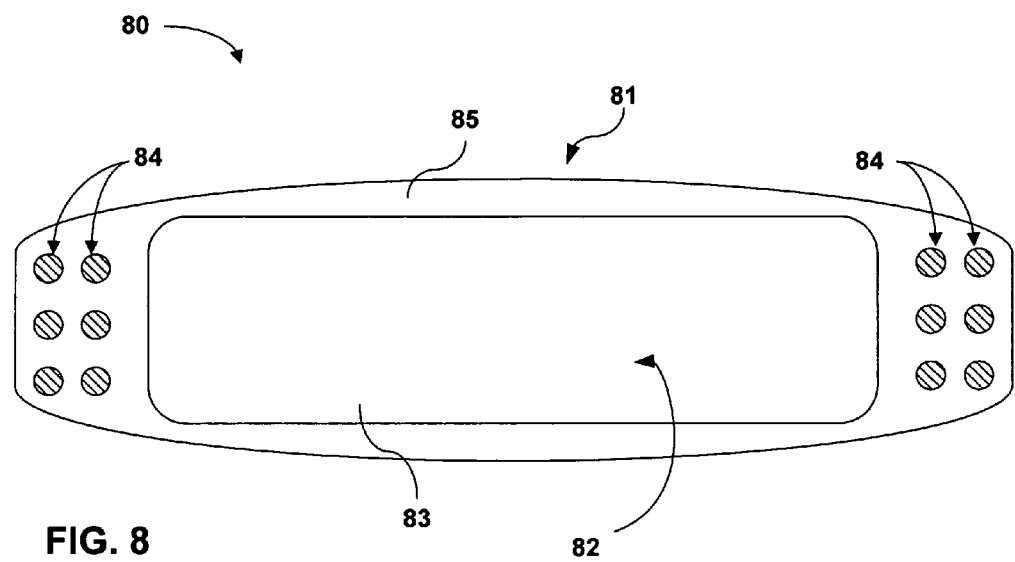
FIG. 8 is a schematic diagram illustrating a bottom view of another example implantable medical device with electrodes located on multiple housing surfaces, in which the housing includes relatively rigid and relatively flexible portions.

FIG. 8 is a schematic diagram illustrating a bottom view of another example IMD 80 in accordance with an embodiment of the invention. IMD 80 comprises a housing 81 that includes a rigid portion 83 and a flexible member 85, such as an overmold, that at least partially encapsulates rigid portion 83. IMD 80 also includes an array of electrodes 84 integrated on flexible member 85 at opposing ends of a bottom surface 82 of housing 81. Each of electrodes 84 may be coupled to a control module (not shown in FIG. 8) within rigid portion 83. At least a portion of each of electrodes 84 protrudes through flexible member 85 for contact with one or more tissues within a patient.

While FIG. 8 illustrates electrodes 84 on the bottom surface 82 and flexible member 85, other embodiments of IMD 70 includes electrodes 84 disposed on one or more other surfaces of housing 81, such as a top surface. Further, IMD 80 may include electrodes 84 on rigid portion 83 instead of or in addition to the flexible member. FIG. 8 also illustrates electrodes 84 grouped into clusters at the ends of surface 82, rather than extending across substantially the entire length or across substantially the entire area of surface 82.

Rigid portion 83 of housing 81 may be formed of any of the rigid housing materials discussed above, such as titanium or stainless steel. Rigid portion 83 may be hermetic and house a control module and battery (not shown). A coil (not shown) for IMD 80 may be located within rigid portion 83 or flexible member 85. Locating the coil within flexible member 85 may improve the communication and energy transfer characteristics of coil by avoiding communication and energy transfer though rigid portion 83. The coil may, for example, substantially encircle rigid portion 81.

Flexible member 85 may comprise a substantially flexible polymer with tapered edges. Flexible member 85 may increase the area of top and bottom housing surfaces 82 without significantly increasing the overall thickness of housing 81. In this way, flexible member 85 may allow more flexibility in the placement of electrodes 84 than integrating the electrodes into a rigid housing alone. Furthermore, flexible member 85 may provide a relatively smooth transition from rigid portion 83 to the tissue surrounding IMD 80. Although IMD 80 has a larger volume than an IMD without a flexible member, e.g., IMD 70, flexible member 85 may improve cosmesis and prevent erosion of the epidermal region adjacent the implantation site of IMD 80.

Electrodes have generally been illustrated herein as being raised from the exterior surface of an IMD housing, such that the electrodes and the housing surface are not flush. However, it may be beneficial to utilize electrodes that have a small thickness to limit the extension of the electrodes into the surrounding tissue area. Further, electrodes 84 may be recessed slightly into the IMD housing to reduce the thickness of the housing.

Figure 9:
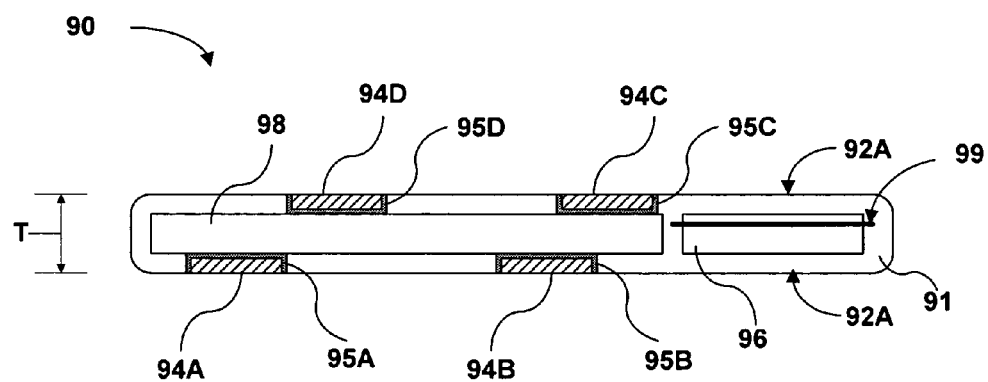
FIG. 9 is schematic diagram illustrating a side cross-sectional view of another example implantable medical device with electrodes located on multiple housing surfaces, in which the electrodes are recessed into the housing surfaces.

For example, FIG. 9 is schematic diagram illustrating a side cross-sectional view of another example IMD 90 with recessed electrodes. As shown in FIG. 9, IMD 90 includes housing 91 with first and second surfaces 92A and 92B, a control module 96, coil 99, battery 98, and electrodes 94A, 94B, 94C and 94D (collectively "electrodes 94") located on first and second surfaces 92A and 92B. IMD 90 and these components may be significantly similar to the other IMDs and components described herein. However, electrodes 94 are recessed within housing 91 such that an exterior surface of each electrode is substantially flush with one of surfaces 92A and 92B. The recessing of electrodes 94 within housing 91 may reduce the thickness (T) of IMD 90 relative to the thickness (T) of, for example, IMD 14 depicted in FIG. 3B.

In order to accommodate electrodes 94, housing 91 may include insulation 95A-D disposed around each of electrodes 94 to electrically separate each electrode from the housing. Insulation 95A-D prevents electric current from being conducted through or along the surface of housing 91, or otherwise effecting the operation of IMD 90. Insulation 185 may be constructed of any material that does not conduct electricity, e.g., rubber, plastic, or composite materials.

Figure 10:
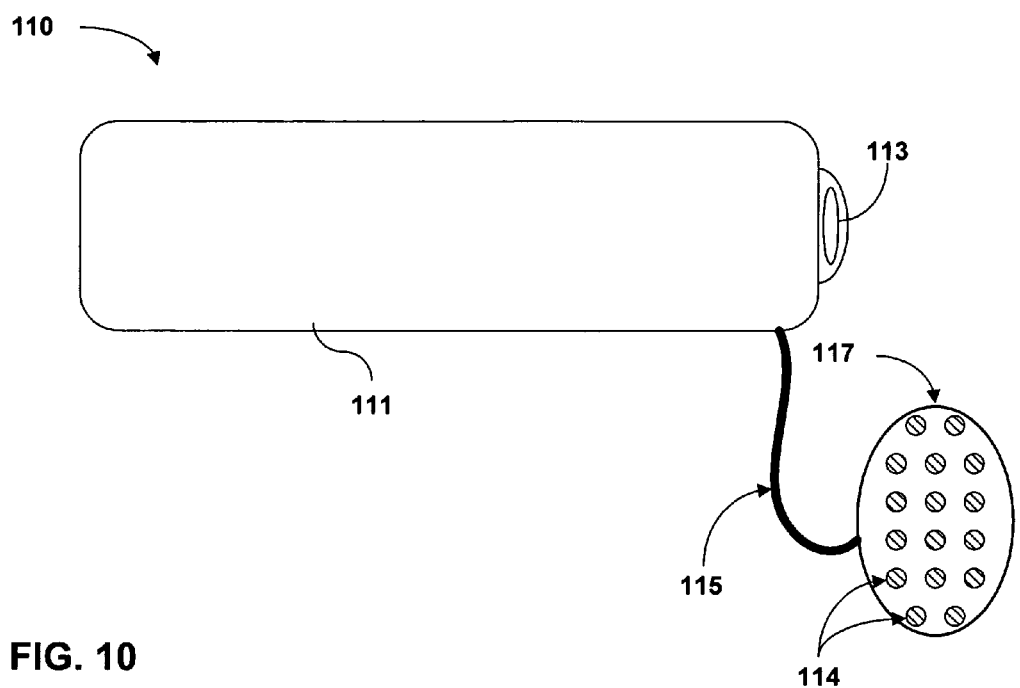
FIG. 10 is schematic diagram illustrating another example implantable medical device coupled to an additional array of electrodes.

FIG. 10 is a schematic diagram illustrating a bottom view of another example IMD 110 in accordance with an embodiment of the invention. IMD 110 comprises a housing 111, and may include electrodes (not shown) on multiple surfaces of the housing, similar to the other IMDs described above. IMD 110 may also include a control module, battery and coil, the other IMDs described above. However, like the IMDs described above, housing 111 includes an attachment mechanism 113 allowing a clinician or physician to secure IMD 110 within a tissue region with suture, staples, or another securing device. In some embodiments, attachment mechanism 113 may be a self-deploying or passive fixation element that protrudes from housing 111 to engage tissue, such as hooks, barbs, screws, expandable stent-like elements, or expandable hydrogel elements. These fixation elements may be in the plane of housing 11 or at some angle to the plane.

IMD 110 further includes a separate member 117 coupled to IMD 110 via a lead 115. Member 117 may support an array of electrodes 114 on one or more of its surfaces. In this manner, IMD 110 may be capable of providing PNFS or other types of electrical stimulation to two or more tissue areas that cannot simultaneously be directly contacted by housing 111.

Further, separate member 117 may be able to be tunneled to a tissue area that is not reachable through direct implantation of IMD 110 or too small to accommodate the IMD.

Figure 11:
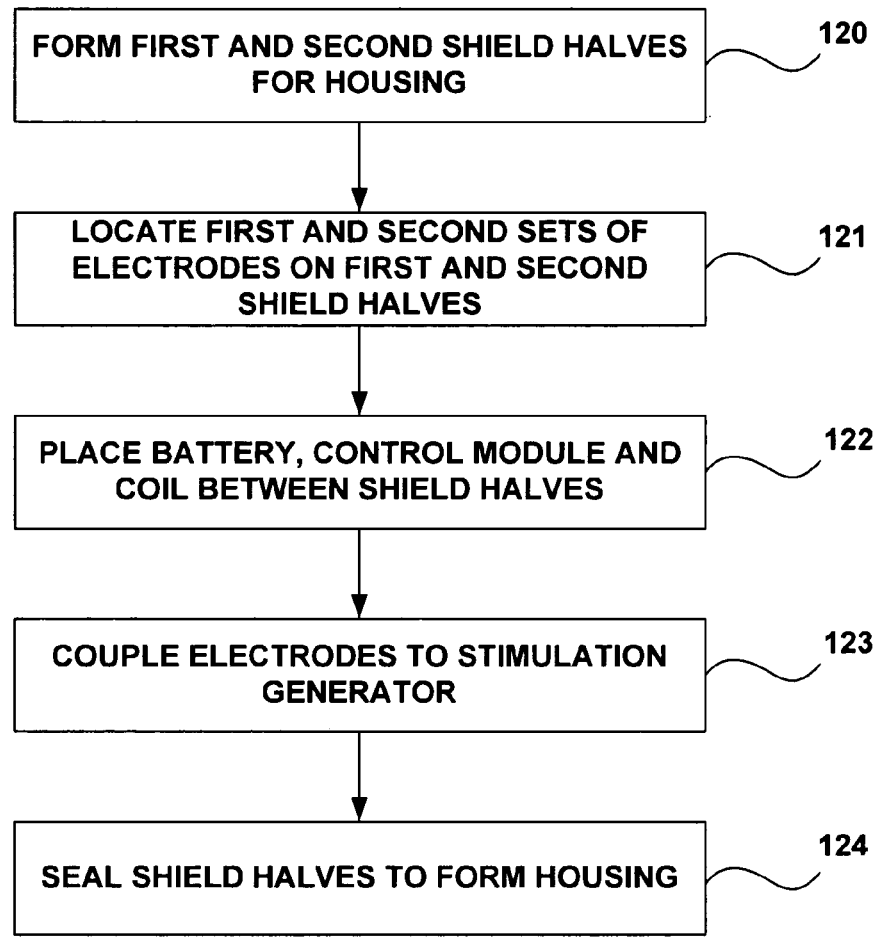
FIG. 11 is a flow diagram illustrating an example method of manufacturing an implantable medical device with electrodes located on multiple housing surfaces.

FIG. 11 is a flow diagram illustrating an example method of manufacturing an IMD with electrodes located on multiple housing surfaces. According to the example method, first and second shield halves, e.g., shallow drawn titanium shield halves, are formed (120). The shield halves respectively include a top or bottom surface for the IMD housing, and may be formed to be concave or convex, or to have an angle, as described above.

First and second sets of electrodes are located on the respective surfaces provided by the shield halves (121). The electrodes may be welded or otherwise attached to the shield halves, or formed thereon by any process, e.g., a deposition process. Locating electrodes on the shield halves may include forming feedthroughs and then adding them through the shield halves for each of the electrodes, forming recess for the each of the electrodes in the shield halves, and placing insulative material on the shield halves for each of the electrodes, e.g., within the recesses.

A battery, control module and coil for the IMD may be placed between the shield halves (122). The electrodes, and more particularly the feedthrough conductors coupled to the electrodes, may be coupled to a stimulation generator, which may be provided by the control module (123). Coupling of the feedthrough conductors may be accomplished by welding or bonding. In some embodiments, a flex-tape circuit may be used to couple the feedthrough conductors to the control module. Insulation may be placed between the shield halves, which may then be hermetically sealed to form the housing for the IMD, e.g., by welding or brazing (124).

Figure 12:
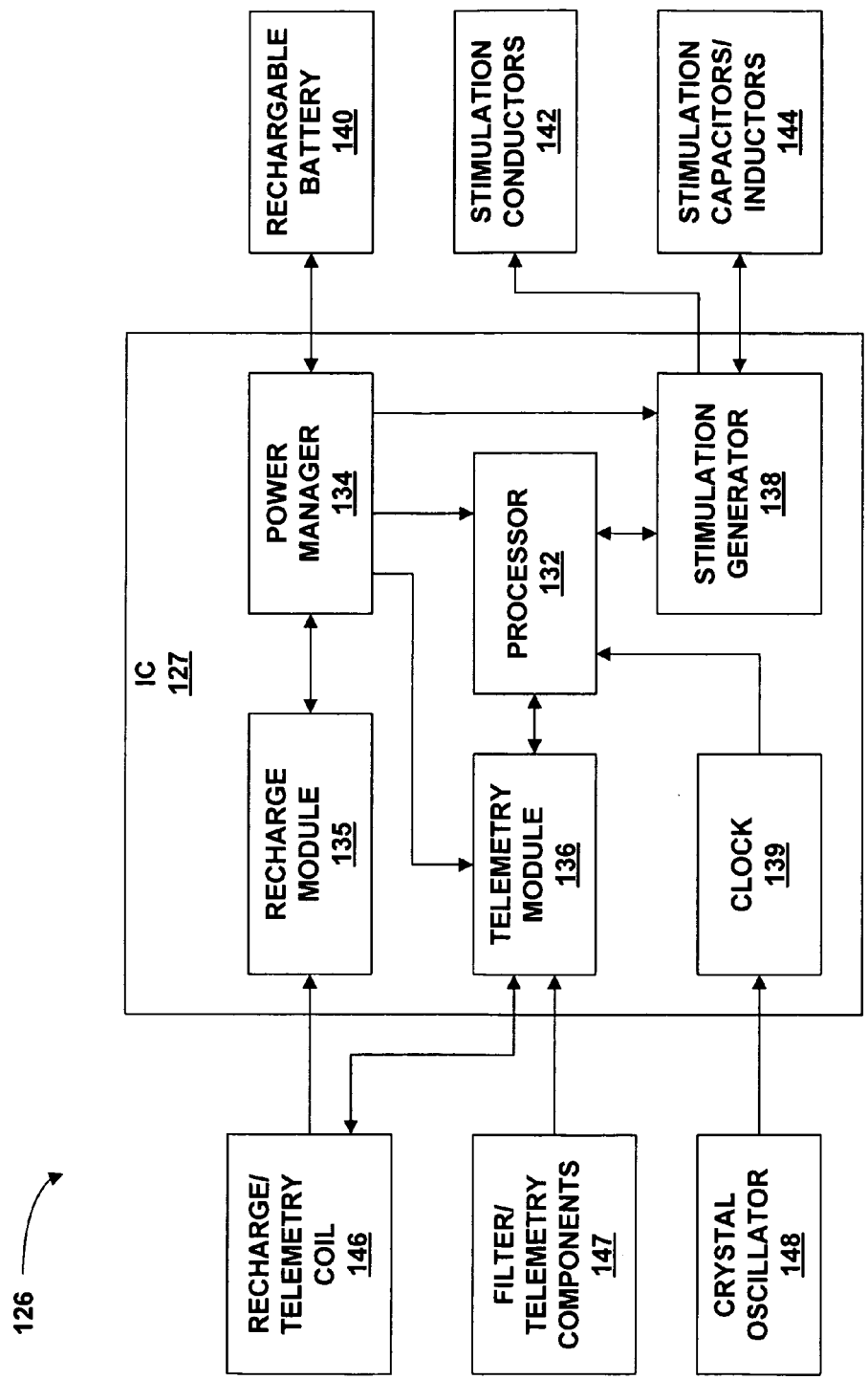
FIG. 12 is a block diagram illustrating an example control module for an implantable medical device with electrodes located on multiple housing surfaces.
Figure 13:
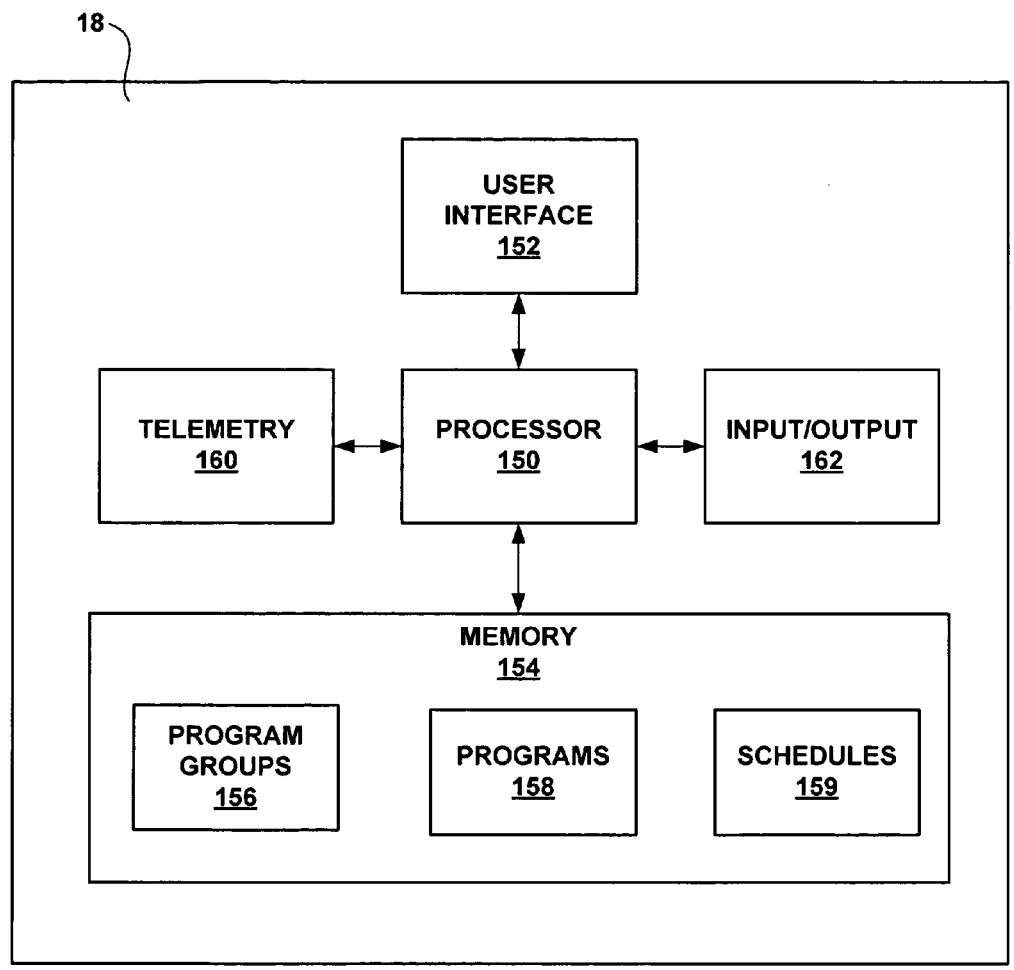
FIG. 13 is a block diagram illustrating an example clinician programmer that allows a clinician to communicate with an implantable medical device.

FIG. 12 is a block diagram illustrating an example control module 126 included in an IMD, which may correspond to control module 46 of IMD 40 depicted in FIGS. 4A and 4B, or any of the other control modules discussed above. Control module 126 comprises an IC 127, stimulation capacitors and inductors 144, filter and telemetry components 147, and a crystal oscillator 148 positioned on a substrate board. The substrate board may comprise a minimal number of layers, e.g. four layers or less, and comprise a thickness equal to or less than approximately 0.4 mm (0.014 inches). Control module 126 is also coupled to a rechargeable battery 140, stimulation conductors 142 that connect to one or more stimulation electrodes of the IMD, and a recharge and telemetry coil 146.

IC 127 may be formed as an ASIC designed to minimize the number of components within the IMD. IC 127 may be designed using the 0.8 micron process in an effort to reduce the overall size and profile of the IMD. IC 127 may operate substantially similar to IC 47 of control module 46 (FIG. 4A). IC 127 includes a processor 132, a power manager 134, a recharge module 135, a telemetry module 136, a stimulation generator 138, and a clock 139.

Power manager 134 couples to rechargeable battery 140 to provide power to processor 132, recharge module 135, telemetry module 136, and pulse generator 138. Recharge module 135 couples to recharge and telemetry coil 146 and receives power via the coil to recharge battery 140. Telemetry module 136 also couples to recharge and telemetry coil 146 and receives stimulation programs and other instructions from a programmer operated by the patient or physician via coil 146. Filter components 147, power manager 134, and telemetry components 147 couple to telemetry module 136 to support reliable wireless communication. Filter and telemetry components 147 may be selected from Table 2 below.

TABLE 2

| Component | Characteristics |
| --- | --- |
| BPLUS Filter | 1 uF |
| VREG Filter | 0.1 uF |
| VDD Filter | 0.1 uF |
| Battery Bypass | 0.1 uF |
| Shottky Diode | — |
| Telemetry Tank Cap | 1500 pF |

Examples of filter, power management and telemetry components include a telemetry tank capacitor, voltage regulation filters, power supply filters, and battery bypass capacitors. Telemetry module 136 provides stimulation programs and other information received from programmers 16, 18 to processor 132, which stores the programs in a memory (not shown). As discussed above with reference to FIGS. 3A and 3B, the memory may also store program instructions that, when executed by processor 132, cause processor 132 to provide the functionality generally ascribed to processors, control modules and IMDs herein.

Crystal oscillator 148 is coupled to clock 139, which clocks processor 132 to run the stimulation programs. Processor 132 directs stimulation generator 138 to provide stimulation to the electrodes of the IMD via stimulation conductors 142. Processor 132 directs stimulation generator 138 according to the stimulation programs received from telemetry module 136 and/or stored in memory, and the clock cycle received from clock 139. In some embodiments, the memory may stored a plurality of programs, and processor 132 may select one or more programs from the plurality based on a schedule stored in memory or a signal received from a programmer 16, 18 via coil 146 and telemetry module 136.

As discussed above, each program may specify stimulation via a combination of electrodes that includes electrodes on a single surface of an IMD housing, or multiple surfaces of the IMD housing. Accordingly, respective programs may be tailored for stimulation of respective tissues or tissue layers via electrodes in respective locations or on respective surfaces, or a program may simultaneously stimulate multiple tissues and tissue layers. In some embodiments, processor 132 may control stimulation generator 138 to deliver stimulation according to a group of programs, each program including a respective electrode configuration involving one or more housing surfaces. Stimulation generator 138 may alternate delivery of stimulation according to the respective programs of the program group, e.g., may deliver each pulse according to a different one of the program, such that the patient cannot perceive transitions between the different programs. The memory of control module 126, which may be on or off IC 127, may store program groups received from programmers 16, 18, and processor 132 may select a program group, in the manner described above.

Stimulation generator 138 may be a voltage or current pulse generator, and may be coupled to stimulation capacitors and inductors 144, which include capacitors to store energy for stimulation pulses. Stimulation generator 138 may control a switching matrix (not shown) to couple stimulation capacitors and inductors 144 to selected electrodes via their corresponding stimulation conductors 142, as directed by a stimulation program. Stimulation capacitors and inductors 144 may contain components provided from Table 3.

TABLE 3

| Component | Characteristics |
| --- | --- |
| Stimulation Cap | 10 uF/20 V |
| Series Stimulation Cap | 10 uF/6 V |
| Bypass Cap | 47 uF/6 V |
| Inductor | 560 uH |

In some embodiments, control module 126 may include more or less components as needed by the IMD containing the control module. For example, multiple memories may be utilized in control module 126. One memory may be used to store operational protocols, one memory may be used to save any error data, and another memory may store stimulation programs for treating the patient. Control module 126 may be configured to conserve energy whenever possible.

Figure 14:
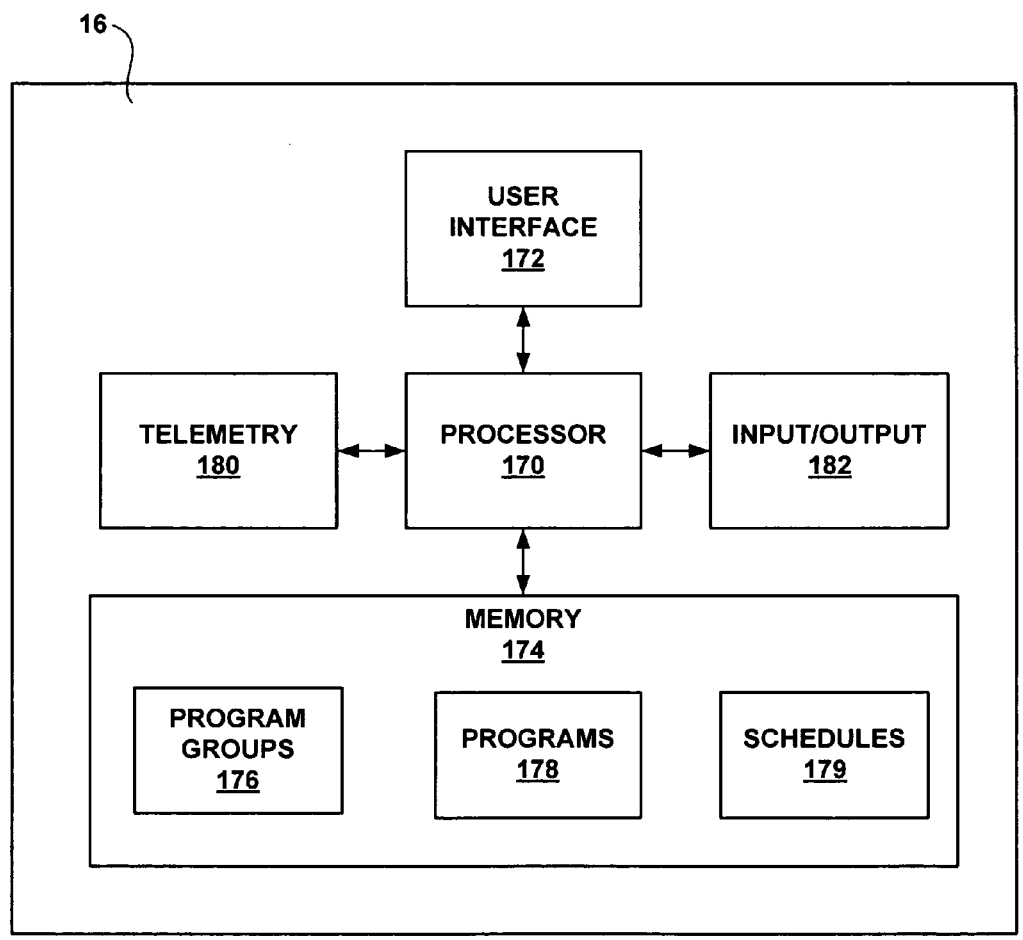
FIG. 14 is a block diagram illustrating an example patient programmer that allows a patient to communicate with an implantable medical device.

FIG. 14 is a block diagram illustrating an example configuration of patient programmer 18. Patient 11 may interact with a processor 150 via a user interface 152 in order to control delivery of stimulation by an IMD, such as IMD 14. User interface 152 may include a display and keypad, and may also include a touch screen or peripheral pointing devices. Processor 150 may also provide a graphical user interface (GUI) to facilitate interaction with patient 11. Processor 150 may include a microprocessor, a controller, a DSP, an ASIC, an FPGA, discrete logic circuitry, or the like.

Patient programmer 18 also includes a memory 154. In some embodiments, memory 154 may store program groups 156 and programs 158 that are available to be selected by patient 11 for delivery of stimulation. Memory 64 may also store schedules 159, which may specify when particular programs 158 or program groups 156 are to be delivered by IMD 14. Memory 154 may also include program instructions that, when executed by processor 150, cause patient programmer 26 to perform the functions ascribed to patient programmer 18 herein. Memory 154 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Patient programmer 18 also includes a telemetry circuit 160 that allows processor 150 to communicate with IMD 14, and input/output circuitry 162 that allows processor 150 to communicate with clinician programmer 16. Processor 150 may receive program or program group selections made by patient 12 via user interface 152, and may either transmit the selection or the selected program or group to IMD 14 via telemetry circuitry 160 for delivery of stimulation by IMD 14 according to the selected program or group. Further, processor 150 may select a program group 156 or programs 158 according to a schedule 159, and may either transmit the selection or the selected program or group to IMD 14 via telemetry circuitry 160 for delivery of stimulation according to the selected program or group. Where patient programmer 18 stores program groups 156 and programs 158 in memory 154, processor 150 may receive program groups 156 and programs 158 from clinician programmer 16 via input/output circuitry 162 during programming by a clinician. Circuitry 162 may include transceivers for wireless communication, appropriate ports for wired communication or communication via removable electrical media, or appropriate drives for communication via removable magnetic or optical media.

Figure 15:
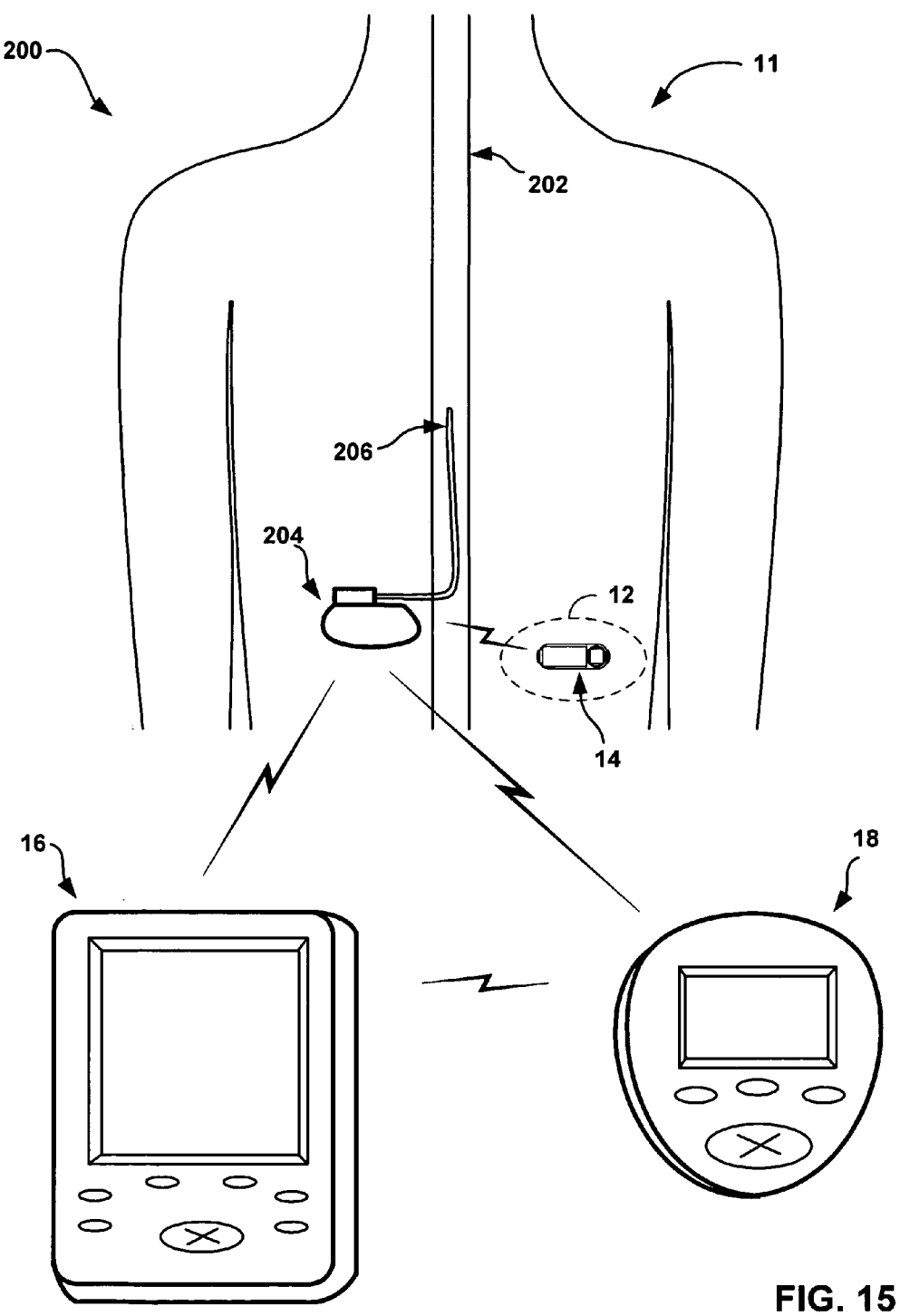
FIG. 15 is a conceptual diagram illustrating another example system that includes an implantable medical device with electrodes on multiple housing surfaces, and additionally includes another implantable medical device for delivery of a combination therapy.
Figure 16A:
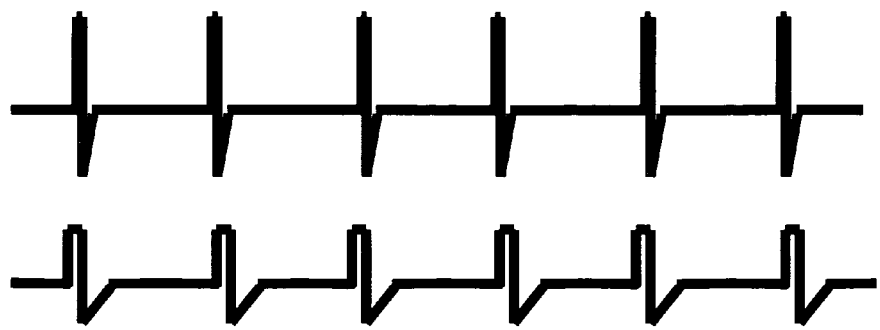
FIGS. 16A-16F are timing diagrams illustrating delivery of two stimulation therapies combination.
Figure 16B:
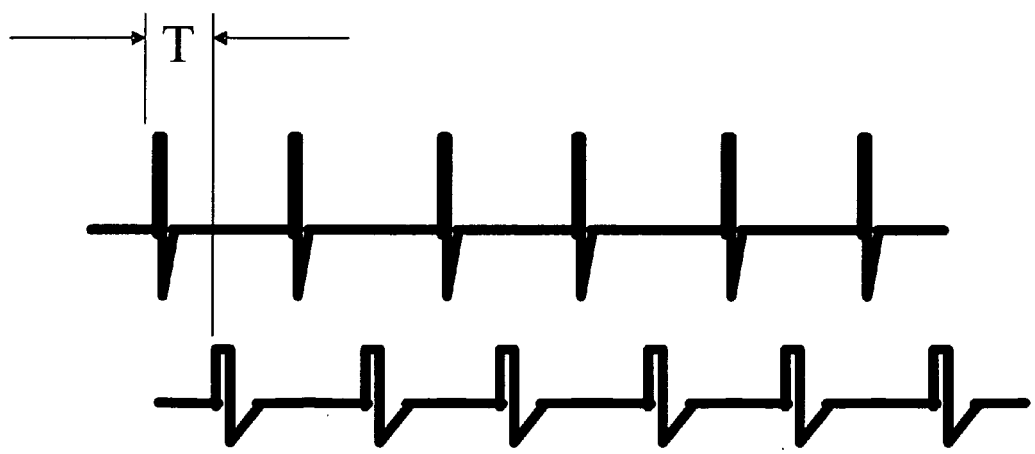
Figure 16C:
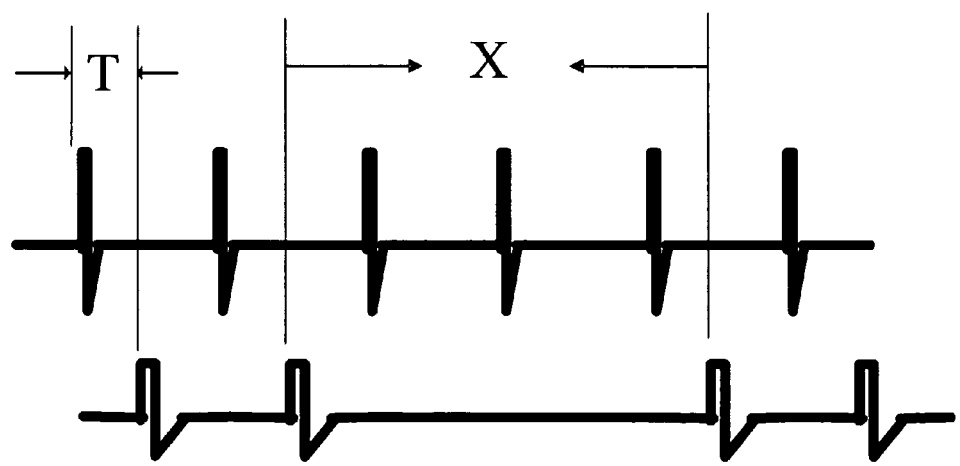
Figure 16D:
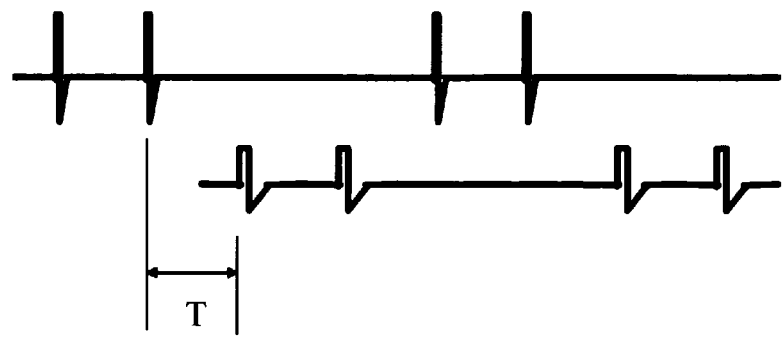
Figure 16E:
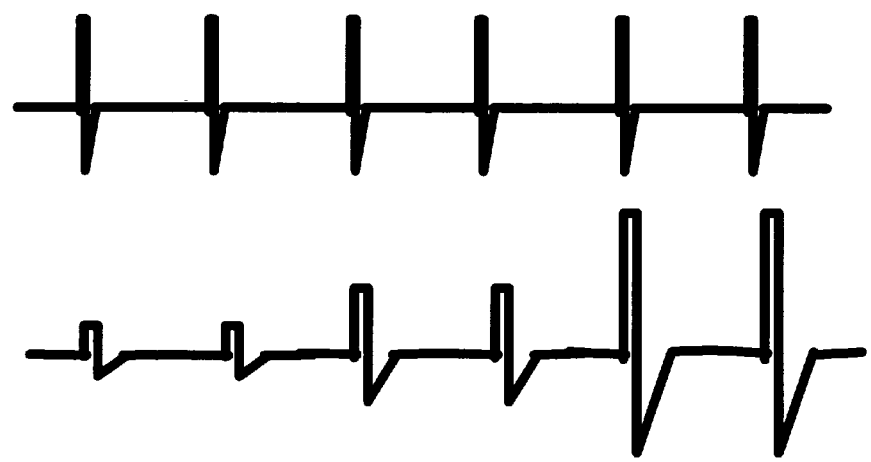
Figure 16F:
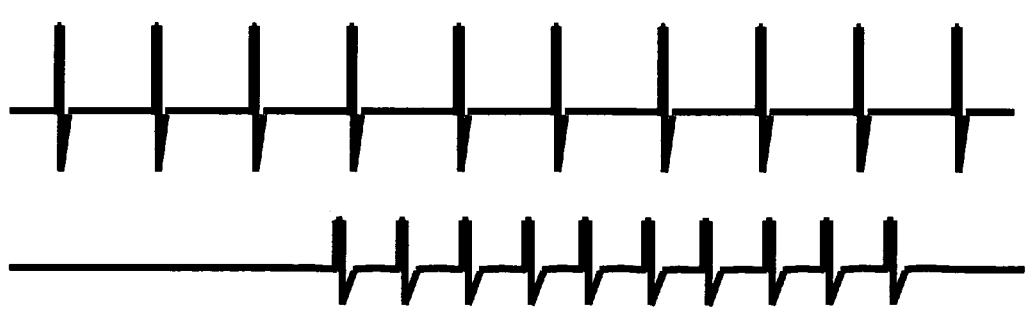

FIG. 15 is a block diagram illustrating an example configuration of clinician programmer 16. A clinician may interact with a processor 170 via a user interface 172 in order to program delivery of stimulation by IMD 14. User interface 172 may include a display and keypad, and may additionally or alternatively include a touch screen or peripheral pointing devices. Processor 170 may also provide a graphical user interface (GUI) to facilitate interaction with a clinician, as will be described in greater detail below. Processor 170 may include a microprocessor, a controller, a DSP, an ASIC, an FPGA, discrete logic circuitry, or the like.

Clinician programmer 16 also includes a memory 174. Memory 174 may include program instructions that, when executed by processor 170, cause clinician programmer 16 to perform the functions ascribed to clinician programmer 16 herein. Memory 174 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

A clinician may program delivery of stimulation for patient 11 by specifying a program group 176 or program 178 to test on patient 11. The clinician may interact with the GUI and user interface 172 in order to specify program groups or programs for testing. Processor 170 transmits the selected or specified programs to IMD 14 for delivery to patient 11 via a telemetry circuit 180.

The clinician or processor 170 may specify an order or protocol for testing of programs. For example, a variety of electrode combinations on a first housing surface of IMD 14 may be tested before proceeding to another housing surface. Electrode combinations involving multiple surfaces may be tested after each surface has been tested individually. Alternatively, electrode combinations involving electrodes on different surfaces may be tested in an alternating fashion to avoid acclimation of any tissue area to the stimulation. Random or idiosyncratic testing orders may also be used.

Processor 170 may transmit program groups 176 and programs 178 selected by the clinician based on the testing, e.g., based on patient feedback, to IMD 14 via telemetry circuitry 180, or to patient programmer 18 via input/output circuitry 182. The clinician may also interact with processor 170 to specify schedules for delivery of therapy, which the processor may transmit to IMD 14 via telemetry circuitry 180, or to patient programmer 18 via input/output circuitry 182. I/O circuitry 182 may include transceivers for wireless communication, appropriate ports for wired communication or communication via removable electrical media, or appropriate drives for communication via removable magnetic or optical media.

FIG. 8 is a diagram illustrating another example system 200 that includes an IMD with electrode located on multiple housing surfaces. System 200 is illustrated as including IMD 14 implanted within region 12 where patient 12 experiences pain, but may include any of the IMDs described above. Unlike system 10 of FIG. 1, however, system 200 includes another IMD 204. IMD 14 and 204 may deliver different therapies, e.g., a combination therapy involving two or more therapies. In some embodiments, as illustrated in FIG. 16, IMDs 14 and 204 may communicate, e.g., wirelessly via radio frequency or body conduction, to coordinate the delivery of their respective therapies.

For example, IMD 14 may deliver PNFS to region 12 in which patient 11 experiences pain, and separate IMD 204 may deliver another type of therapy to treat pain. Through delivery of a combination therapy that includes PNFS and one or more other types of therapy, system 200 may be able to more completely address complex or multifocal pain than would be possible through delivery of either PNFS or the other therapies alone. In addition, the combination of PNFS with one or more other types of therapy may reduce the likelihood that neural accommodation or plasticity will impair the perceived effectiveness of any of the therapies.

IMD 204 may deliver another neurostimulation therapy in combination with the PNFS delivered by IMD 14. In the illustrated embodiment, IMD 204 delivers spinal cord stimulation (SCS) to the spinal cord 202 of patient 12 in combination with delivery of PNFS. IMD 204 delivers SCS via electrodes located on one or more leads 206 implanted proximate to spinal cord 202.

The electrodes may be implanted in, for example, an epidural space or proximal to the dorsal root entry zone of patient 11. In some embodiments, the electrodes are located within a region defined by vertebral levels T7-L1. For example, lead 206 may be implanted in the epidural space near vertebral levels T8-T10 to treat axial back pain, over the dorsal roots of L3-S1, over the dorsal columns at vertebral levels T10-L1 to treat pain in the ankle or foot, or near vertebral levels T9-T11 give paresthesia to the entire thigh. SCS may be most effective at treating neuropathic pain, such as neuropathy or radiculopathy that involves a substantial portion of one limb and more than one dermatome.

However, the invention is not limited to embodiments in which lead 206 extends to spinal cord 202, or IMD 204 delivers SCS. In other embodiments, an IMD may deliver one or more of peripheral nerve stimulation (PNS), deep brain stimulation (DBS) and cortical stimulation (CS) in combination with PNFS. SCS, PNS, DBS and CS are examples of other neurostimulation therapies that may be delivered in combination with PNFS. In such embodiments, IMD 204 and leads 206 may be implanted at locations appropriate for delivery of such therapies.

For example, lead 206 may extend to a location closely proximate to a particular peripheral nerve responsible for causing patient 11 to experience pain, and IMD 204 may deliver peripheral nerve stimulation (PNS) to the peripheral nerve. In still other embodiments, lead 206 may extend to the brain of patient 12 (not shown) via a hole formed in the cranium of the patient, and IMD 204 may deliver deep brain stimulation (DBS) or cortical stimulation (CS). For DBS, electrodes may be implanted within the brain, and for CS, electrodes may be implanted within or proximate to the brain. Multiple leads 206 may extend from IMD 204 to one or more such locations for delivery of SCS, DBS, CS, PNS or other neurostimulation therapies. For example, two leads 206, each with eight electrodes may extend to spinal cord 202.

System 200 may deliver PNFS in combination with other types of therapy in order to address complex or multifocal pain. Many cases of axial pain are complex, i.e., both neuropathic (prior nerve injury) and nociceptive (ongoing stimuli). Additionally, a patient may have pain localized in a small area that is uniformly unresponsive to SCS or PNS. For example, a patient may experience arthritis pain in part of one limb, trunkal pain of post-herpetic neuralgia (PHN), or limb pain from advanced complex regional pain syndrome (CRPS) after trophic changes are irreversible. Current advanced pain management therapies for neuropathic pain, nociceptive pain, and/or axial pain may have effective treatment for a portion of the pain experienced by patient 11, but do not always relieve a patient from their pain entirely. For example, when delivering only SCS, the patient may still experience nociceptive pain since SCS only treats neuropathic pain.

As an example, patients with failed back surgery syndrome (FBBS) often have both axial pain due to pressure, instability, inflammation and nerve damage near the vertebra, and radiculopathy down one or both legs due to prior damage to nerve roots. Typically, only one modality of therapy, such as stimulation or drugs, is used since each modality has an implanted device that has its own advantages and disadvantages. Consequently, a physician may pick the modality that treats the worst pain even though pain location, nature, intensity, and other pain characteristics may change over time.

For example, SCS delivered via a set of electrodes at vertebral levels T8-T10 may be used to treat axial pain and, in some cases, may even give paresthesia into parts or all of the legs. However, such SCS stimulation often cannot give paresthesia into the feet, since fibers ascending in the dorsal columns from feet are small and possibly deep at the midthoracic levels. Thus, another set of electrodes may be implanted over the dorsal roots at L3-S1, or over the vertebral levels T10-L1. However, the relief of axial pain may fade over a period of time because even with delivering stimulation to different areas of the spinal cord the patient may focus on the remaining axial pain and may be relatively dissatisfied.

Furthermore, even if a patient has only axial back pain, or pain in a localized region of the trunk, using only one modality of stimulation may not be sufficient to relieve a substantial amount of the pain experienced by the patient. Moreover, SCS alone has a limitation for pain in the upper arms and neck since leads placed in the epidural space at the upper thoracic and cervical vertebral levels often move significantly relative to the spinal cord. Consequently, the level of paresthesia can change dramatically thereby preventing sleep or use during normal movements.

In addition, the nervous system has many parallel paths that communicate sensations, including pain, to the brain. Examples of such paths include the lateral spinothalamic paths, the dorsal columns (especially for visceral pain), the spinoreticular paths (for alerting), and spinocerebellar paths. When one of the paths is interrupted to diminish pain, the pain often eventually returns via another pathway.

System 200 can deliver PNFS in combination with other therapies to affect different brain and spinal areas separately. In particular, delivering PNFS in combination with one or more other therapies may provide a synergistic effect by targeting different portions of the neural "circuit" thereby reducing the likelihood that neural accommodation will reduce the efficacy of one of the therapies. Thus, delivering PNFS in combination with one or more other therapies may more completely address complex pain than would be possible through delivery of either PNFS or the other therapies alone.

The invention is not limited to embodiments in which the other therapy that treats pain is a type of neurostimulation. In some embodiments, for example, IMD 204 may deliver a drug or other therapeutic agent in combination with the PNFS delivered by IMD 14. In such embodiments, IMD 204 may include a reservoir and pump, and be coupled to a catheter that extends to a target location for delivery of the therapeutic agent.

For example, the catheter may extend from IMD 204 to spinal cord 202, and delivers the one or more drugs intrathecally, although the invention is not limited as such. Alternatively, the catheter may extend to any extra-dural location, including region 12. IMD 204 may be coupled to any number of catheters that extend to any number of locations.

Examples of therapeutic agents that IMD 204 may deliver in combination with the delivery of PNSF by IMD 14 are opioids, cannabinoids, anti-inflammatory agents, steroids, baclofen, adenosine, local anesthesia, anti-depressants, and alpha agonists. Delivered agents may, for example, diminish pain by their own action, especially when applied to specific sites, enhance the benefits of electrical stimulation, and treat particular pain modalities. Nociceptive pain may be treated through delivery of morphine, for example, and the action of specific nerves may be blocked through delivery of local anesthetics. Consequently, delivering PNFS in combination with drug therapy may more completely address complex pain than would be possible through the delivery of one of the other therapies alone.

Further, the invention is not limited to embodiments with two implanted devices to deliver the combination therapy. For example, more than two devices may deliver the combination therapy, or IMD 14 deliver the combination therapy, e.g., via attached leads or catheters. Also, an external device may deliver a therapy, such as transcutaneous electrical neurostimulation (TENS), in combination with the delivery of PNFS by IMD 14.

Alternatively, other delivery mechanisms, such as a patch or other transdermal delivery mechanism, or oral consumption by a patient, may be used for a combination therapy including a therapeutic agent. For example, patient 11 may absorb drugs through a patch at region 12 to further relieve pain experienced at region 12 or enhance the PNFS therapy. As one example of the synergy between therapies, PNFS delivered to region 12 by IMD 14 may reduce allodynia, thereby allowing a patch to be applied to the skin of patient 11 to deliver drug therapy.

System 200 may deliver PNFS in combination with other types of therapy simultaneously, or in an interleaved or alternating fashion. For example, when the combined therapies include a plurality of electrical stimulation therapies, IMDs 14 and 204 may deliver electrical pulses according to each of the therapies in an alternating or interleaved fashion, e.g., each pulse delivered according to a different one of the therapies. Consequently, the delivery of each therapy can be optimized at each site.

The different electrical stimulation therapies may have different pulse rates, duty cycles, or scheduled times for delivery, which may result in alternating delivery of therapies. Thus, electrical pulses can be interleaved so as to deliver the same frequency of electrical pulses to respective sites, but with varying amplitudes or pulse widths. Alternatively, a packet of pulses may be delivered to a PNFS site, with or without ramping of amplitude from start to finish, followed by delivering another packet of pulses to, for example, a SCS site.

Interleaved or alternating delivery of PNFS and one or more other electrical stimulation therapies may, for example, reduce the likelihood that neural accommodation or plasticity will impair the efficacy of one or more of the therapies, while still providing therapy at any given time. In particular, avoiding constant stimulation at a site, PNFS or otherwise, may prevent neural accommodation that would reduce the efficacy of one or more of the therapies. Interleaved or alternating deliver of PNFS and one or more other electrical stimulation therapies may also prevent overuse or depletion of transmitters, such as GABA-B, that are major inhibitory transmitters released in the dorsal horn when electrical stimulation produces pain relief. Further any or all of the combined therapies may be delivered selectively, e.g. upon request by a user, such as a physician or a patient. In other words, system 200 may provide multiple therapies that may be selected by a user, e.g., as the pain experienced dictates, but need not deliver a plurality of therapies at all times.

A clinician (not shown) may use clinician programmer 16 to program PNFS by communicating with IMD 14, and the at least one other therapy for patient 11 by communicating with IMD 204. In particular, the clinician may use clinician programmer 16 to select values for therapy parameters, such as pulse amplitude, pulse width, pulse rate, electrode polarity and duty cycle, for both the PNFS and the other therapy. Infusion rate, concentration, ratio (if two or more drugs are delivered), and duty cycle are examples of therapy parameters for drug delivery. IMDs 14 and 204 may deliver the PNFS and the other therapy according to respective programs or groups of programs, each program including respective values for each of a plurality of such therapy parameters. The clinician may identify preferred programs for PNFS and one or more other therapies separately, or through delivery of the therapies together. In some embodiments, varying the pulse frequency may allow PNFS to capture target nerve fibers, such as small, medium, or large fibers sensitive to pulse frequency.

System 200 also includes patient programmer 18, which patient 11 may use to control the delivery of PNFS and the at least one other therapy by IMDs 14 and 200. Patient 12 may use patient programmer 18 to activate or deactivate PNFS, the one or more other therapies, or both, and may use patient programmer 18 to select the programs or program group that will be used by IMDs 14 and 204 to deliver PNFS in combination with one or more other types of therapy. Further, patient 11 may use patient programmer 18 to make adjustments to programs or program groups. Additionally, the clinician or patient 11 may use programmers 16, 18 to create or adjust schedules for delivery of PNFS, the one or more other therapies, or both.

The respective rates, duty cycles, or schedules for PNFS and the one or more other therapies of a combination may facilitate alternating delivery of PNFS and the one or more other therapies. Further, IMDs 14 and 204 may communicate to coordinate alternating delivery of the therapies. In other embodiments, the IMDs 14 and 204 may deliver their therapies simultaneously, or both simultaneously and at different times without any coordination.

FIGS. 17A-17F are timing diagrams illustrating delivery of PNSF in combination with another neurostimulation therapy according to embodiments of the invention. SCS, PNS, DBS, and CS are examples of other types of neurostimulation therapies that may be delivered in combination with PNFS. In general, IMDs 14 and 204 may deliver electrical pulses according to each of the therapies simultaneously, in an interleaved or alternating fashion, or overlapping in some degree in time. For example, each electrical stimulation therapy may have different pulse rates, duty cycles, or scheduled times for delivery, each of which may result in an alternating delivery of the therapies. In each of FIGS. 17A-17E, the bottom group of pulses represents delivery of PNFS pulses by IMD 14, and the top group of pulses represents delivery of another neurostimulation therapy, such as SCS, by IMD 204. In FIG. 17F, the top group of pulses represents delivery of PNFS pulses by IMD 14, and the bottom group of pulses represents delivery of another neurostimulation therapy, such as DBS, by IMD 204. Each group of pulse may represent delivery of pulses by IMDs 14 and 204 according to a respective therapy program, and both groups of pulses may be included in a respective program group.

FIG. 17A illustrates simultaneous delivery of PNFS and another neurostimulation therapy at a common pulse rate of 50 Hz by IMDs 14 and 204. However, the PNFS and other neurostimulation are delivered with different amplitudes and pulse widths. Specifically, in the example illustrated by FIG. 17A, pulse for the other neurostimulation is delivered with a pulse amplitude and pulse width of 3 volts and 150 µs, respectively, and PNFS pulses are delivered at a pulse amplitude and pulse width of 2 volts and 300 µs, respectively.

FIG. 17B illustrates interleaved delivery of PNFS and another neurostimulation therapy by IMDs 14 and 204 at the common pulse rate and different pulse amplitudes and widths illustrated by FIG. 17A. Interleaved delivery of PNFS pulses and pulses for the other neurostimulation resulting in a phase offset represented by a time T.

As was the case with FIG. 17B, FIG. 17C illustrates interleaved delivery of PNFS and another neurostimulation therapy by IMDs 14 and 204 at the common pulse rate and different pulse amplitudes and widths illustrated by FIG. 17A. However, in the example illustrated by FIG. 17C, IMD 14 delivers PNFS according to a duty cycle, rather than continuously. As a result, PNFS and the other neurostimulation are delivered for in an interleaved fashion similar to FIG. 17B for a period of time, followed by an equal period of time in which only the other neurostimulation is delivered.

FIG. 17D illustrates delivery of both PNFS and the other neurostimulation according to respective duty cycles, where the duty cycles result in alternating delivery of PNFS and the other neurostimulation.

FIG. 17E illustrates an example in which IMD 14 increases, e.g., "ramps up," the pulse amplitude of PNFS over time. In particular, FIG. 17E illustrates a pulse amplitude increase every two pulses FIG. 17F illustrates delivery of PNFS and another neurostimulation therapy by IMDs 14 and 204 according to different therapy parameters. In particular, IMD 14 delivers pulses for PNFS (top) at a frequency, amplitude, and pulse width of 40 Hz, 4.8 volts, and 400 μs, respectively, and IMD 204 delivers pulses for the other neurostimulation therapy (bottom) at a frequency, amplitude, and pulse width of 240 Hz, 2 volts, and 60 μs, respectively.

Table 4 below illustrates various combinations of PNFS therapy with other types of therapy to relieve pain associated with a number of conditions. In particular, each row of the table provides an "indication" that is treated, a location or "site" at which to deliver PNFS, reason(s) for delivering PNFS at the site, various sites at which to deliver other therapies and the reasons for delivering the other therapy types. The other types of therapy delivered in combination with PNFS include SCS, PNS, and various forms of DBS and CS. The acronyms PVG and PAG refer to midbrain gray matter stimulation locations, and the acronyms VPL and VPM refer to thalamic stimulation location. More particularly, PVG, PAG, VPL and VPM respectively refer to a preventricular gray, periaqueductal gray, ventroposterior lateral nucleus and ventral posterior medial nucleus stimulation locations.

For example, PNFS may be delivered in combination with SCS, PNS, DBS and/or CS to treat axial back pain. In this case, 1-4 leads having 4-64 electrodes may be implanted in the intra-dermal, deep-dermal, or subcutaneous tissue at region where the patient experiences pain. SCS may be delivered to the T7-T10 vertebral levels in combination with PNFS to give paresthesia into the back. PNS may be delivered to a branch of the median nerve in combination with PNFS to treat facet pain that the patient may experience in addition to the axial back pain. DBS may be delivered to PVG, PAG, or VPL locations in combination with PNFS to treat neuropathic components of the pain. CS may also be delivered to the motor cortex, near the midline in combination with PNFS to treat neuropathic components.

As another example, PNFS may be delivered in combination with SCS, DBS and/or CS to treat occipital neuralgia and headaches. In this case, electrode groups for PNFS may be implanted in a line transverse to the C2 and C3 nerve branches. Fascia, muscle, or tendons may be between the groups of electrodes and the nerves in order reduce the likelihood of unpleasant stimulation. SCS may be delivered to the C1-C3 nerves in combination with PNFS to give paresthesia into the back. DBS may be delivered to PVG, PAG, or VPM locations in combination with PNFS to treat neuropathic components of the pain, or triggers of the migraines. CS may be delivered to the lateral part of the motor cortex in combination with PNFS to also treat neurpathic components or triggers.

In another example, PNFS may be delivered in combination with PNS, DBS and/or CS to treat temporomandibular join pain. In this case, electrodes for PNFS may be implanted in front of the ear to deliver stimulation to or near the region where the patient experiences pain. PNS may be delivered to branches of the trigeminal nerve (V), including delivering PNS in the Gasserian ganglia foramen, in combination with PNFS to relieve neuropathic pain. DBS may be delivered to PVG, PAG, or VPM locations in combination with PNFS to give paresthesia into the face of the patient. CS may be delivered to the lateral part of the motor cortex in combination with PNFS to treat neurpathic components of the pain.

A common patient problem for stimulation therapies today is a combination of axial back pain and radiculopathy, which is often a form of failed back surgery syndrome (FBBS). In a further example, PNFS may be delivered in combination with SCS, PNS, DBS and/or CS to treat FBBS. SCS can work very well for the radiculopathy, especially for the lower limbs, but its success for the axial pain can be less, especially after six or more months. In this case, PNFS in the painful areas of the back can help the axial pain, and the SCS part of the combined system can deal well with the radicular symptoms.

The following combination of therapies may provide relief from axial pain and radiculopathy associated with FBBS. In this case, 1-4 electrode leads having 4-64 electrodes may be implanted in intra-dermal, deep-dermal, or subcutaneous tissue in a region where the patient experiences pain for delivery of PNFS. SCS may be delivered to the T7-T10 vertebral levels as well as the T10-L1 vertebral levels in combination with PNFS to give paresthesia into the back, leg, and/or foot. DBS may be delivered to PVG, PAG, or VPL locations in combination with PNFS to treat neuropathic components of the pain. CS may be delivered near the midline of the motor cortex in combination with PNFS to treat neurpathic components or triggers.

In yet another example, PNFS may be delivered in combination with SCS, DBS and/or CS to treat supra-orbital or sub-orbital facial pain. In this case, electrode groups for PNFS may be implanted in a line above or below the eye, e.g., roughly parallel to the eyebrow, to deliver stimulation to branches of the facial nerve (VIII). In this case, SCS may be delivered to the C1-C3 nerves in combination with PNFS to give paresthesia into the back of the head and neck. DBS may be delivered to PVG, PAG, or VPM locations in combination with PNFS to treat neuropathic components or triggers. CS may be delivered to the lateral part of the motor cortex in combination with PNFS to treat neurpathic components or triggers.

In a further example, PNFS may be delivered in combination with SCS, PNS, DBS and/or CS to treat arthritis. In this case, electrode groups may be implanted in intra-dermal, deep-dermal, or subcutaneous tissue in any region where the patient experiences arthritis pain. SCS may be delivered to the C4-C8 vertebral levels for upper limb pain and to the T10-L1 vertebral levels for hip, knee, ankle and foot pain in combination with PNFS to give paresthesia into the painful area. PNS may be delivered to an appropriate major arm or leg nerve in combination with PNFS to give paresethesia into the painful area. DBS may be delivered to PVG, PAG, or VPL locations in combination with PNFS to treat neuropathic components or triggers. CS may be delivered near the midline of the motor cortex in combination with PNFS to treat neurpathic components in the leg and feet. CS may also be delivered near the lateral part of the motor cortex in combination with PNFS to treat neurpathic components in the arm and hand.

In another example, PNFS may be delivered in combination with SCS, PNS, DBS and/or CS to treat inguinal pain. In this case, electrode groups may be implanted in intra-dermal, deep-dermal, or subcutaneous tissue in any region where the patient experiences pain to give nonpainful PNFS stimulation to the painful area. SCS may be delivered to the T4-L1 vertebral levels in combination with PNFS to give paresthesia into the painful area. PNS may be delivered via electrodes implanted deeper along the nerves involved in the pain in combination with PNFS to give paresethesia into the painful area. DBS may be delivered to PVG, PAG, or VPL locations in combination with PNFS to treat neuropathic components or triggers. CS may be delivered near the midline of the motor cortex in combination with PNFS to treat neurpathic components in the leg and feet.

In another example, PNFS may be delivered in combination with SCS, PNS, DBS and/or CS to treat arthritis. In this case, electrode groups may be implanted in intra-dermal, deep-dermal, or subcutaneous tissue in any region where the patient experiences pain to give nonpainful PNFS stimulation to the painful area. SCS may be delivered to the T8-L1 vertebral levels in combination with PNFS to give paresthesia into the painful area. PNS may be delivered to the pudendal nerve in combination with PNFS to treat neuropathic components. DBS may be delivered to PVG, PAG, or VPL locations in combination with PNFS to treat neuropathic components or triggers. CS may be delivered near the midline of the motor cortex in combination with PNFS to treat neurpathic components in the lower body.

In another example, PNFS may be delivered in combination with SCS, PNS, DBS and/or CS to treat angina, or pain associated with other heart dysfunction, such as arrhythmia. In this case, electrodes may be implanted over the heart, any part of the thorax or at any region where the patient experiences pain, such as in the arms, jaw, or back. For example, electrodes may be implanted within or between intra-dermal, deep dermal, or subcutaneous tissues of the chest. Delivering PNFS in this manner may reduce angina attacks. SCS may be delivered to the C1-T4 vertebral levels in combination with PNFS to give paresthesia into the painful area and reduce angina. PNS may be delivered to the vagus nerve in combination with PNFS to slow the heart and, thus, reduce stress on the heart. DBS may be delivered to PVG, PAG, or VPL locations in combination with PNFS to treat neuropathic components. DBS may also be delivered to nuclei near the hypothalamus or in the ventral lateral medulla in combination with PNFS to lower blood pressure, which may reduce pain by reducing the stress on the heart. CS may be delivered several centimeters off the midline of the motor cortex in combination with PNFS to treat neurpathic components.

In yet another example, PNFS may be delivered in combination with SCS, PNS, DBS and/or CS to treat cancer pain or phantom limb pain. In this case, electrode groups may be implanted in intra-dermal, deep-dermal, or subcutaneous tissue in a region where the patient experiences pain to give nonpainful stimulation to the painful region. SCS may be delivered at a level appropriate to the pain experienced by the patient in combination with PNFS to give paresthesia into the painful area. PNS may be delivered to a nerve involved in the pain in combination with PNFS to treat neuropathic components of the pain. DBS may be delivered to PVG, PAG, VPL, or VPM locations in combination with PNFS to treat neuropathic components or triggers. CS may be delivered at an appropriate location of the motor cortex in combination with PNFS to treat neurpathic components of the pain.

TABLE 4

| Indication | Site for PNFS | Reason for Delivering PNFS | Site for other Therapy | Reason for Delivering Other Therapy |
|---|---|---|---|---|
| Axial back pain | Axial back, 1-4 leads, 4-64 electrodes | Deliver stimulation to the region where patient experiences pain | SCS: T7-T10 | Gives paresthesia into the back |
| | | | PNS: branch of median nerve | Also treat facet pain |
| | | | DBS: PVG or PAG | Treat nociceptive components |
| | | | DBS: VPL | Treat neuropathic components |
| | | | CS: motor cortex, near midline | Treat neuropathic components |
| Occipital neuralgia, headaches | Electrode groups in a line transverse to the C2 and C3 nerve branches | Deliver stimulation to the C2 and C3 nerves to prophylactically prevent migraines and headaches | SCS: C1-C3 | Gives paresthesia into the back |
| | | | DBS: PVG or PAG | Treat nociceptive components |
| | | | DBS: VPM | Treat neuropathic components or triggers |
| | | | CS: motor cortex, lateral part | Treat neuropathic componenets or triggers |
| Temporomandibular joint pain | In front of ear | Deliver stimulation to or near the pain site. May be | PNS: branches of the trigeminal nerve (V), | Relieve neuropathic pain |

TABLE 4-continued

| Indication | Site for PNFS | Reason for Delivering PNFS | Site for other Therapy | Reason for Delivering Other Therapy |
|---|---|---|---|---|
| | | desirable to avoid nerves in lower jaw | including in the Gasserian ganglia foramen | |
| | | | DBS: PVG or PAG | Treat nociceptive components |
| | | | DBS: VPM | Gives paresthesia into the face |
| | | | CS: motor cortex, lateral part | Treat neuropathic components |
| Failed back surgery syndrome (axial pain and radiculopathy) | Axial back, 1–4 leads, 4–64 electrodes | Deliver stimulation where the patient experiences pain | SCS: T7–L1 | Gives paresthesia into the back and leg and/or foot |
| | | | PNS: Branch of median nerve or along nerves in leg | Also treat facet join pain an neuropathies in the nerves in the leg |
| | | | DBS: PNG or PAG | Treat nociceptive components |
| | | | DBS: VPL | Treat neuropathic components |
| | | | CS: motor cortex, near midline | Treat neuropathic components |
| Supra-orbital or sub-orbital facial pain | Electrode groups in a line above or below the eye, roughly parallel to the eyebrow | Deliver stimulation to branches of the facial nerve (VIII) | SCS: C1–C3 | Gives paresthesia into the back of the head and neck |
| | | | DBS: PVG or PAG | Treat nociceptive components |
| | | | DBS: VPM | Treat neuropathic components |
| | | | CS: motor cortex, lateral part | Treat neuropathic components |
| Arthritis | Place electrodes in skin with the same dermatome as the painful area | Give nonpainful stimulation to the same nerves as those involved in pain | SCS: C4–C8 for upper limb pain; T1–L1 for hip, knee, ankle or foot pain | Gives paresthesia into the painful area which may lessen pain |
| | | | PNS: of the major arm or leg nerves | Gives paresthesia into the painful area which may lessen pain |
| | | | DBS: PVG or PAG | Treat nociceptive components |
| | | | DBS: VPL | Treat neuropathic components |
| | | | CS: motor cortex, near midline for leg and feet | Treat neuropathic components |
| Pelvic pain, and or visceral organ pain | Place electrodes in skin areas over any painful area | Give nonpainful stimulation to painful area | SCS: T8–L1 | Gives paresthesia into the painful area which may lessen pain |
| | | | PNS: Pudendal nerve | Treat neuropathic components |
| | | | DBS: PVG or PAG | Treat nociceptive components |

TABLE 4-continued

| Indication | Site for PNFS | Reason for Delivering PNFS | Site for other Therapy | Reason for Delivering Other Therapy |
|---|---|---|---|---|
| | | | DBS: VPL | Treat neuropathic components |
| | | | CS: motor cortex, near midline for lower body | Treat neuropathic components |
| Angina, heart dysfunction, or arrhythmia | Electrodes over the heart part of the thorax or at any painful area, even in the arms, jaw, or back | Reduce angina attacks | SCS: C1–T4 | Gives paresthesia into the painful area which may lessen pain and reduce angina |
| | | | PNS: Vagus nerve, medial nerve, unlar nerve | Slows heart, reducing stress on the heart |
| | | | DBS: PVG or PAG | Treat nociceptive components |
| | | | DBS: VPL | Treat neuropathic components |
| | | | DBS: Nuclei near the hypothalamus or in the ventral lateral medulla | Lowers blood pressure |
| | | | CS: motor cortex, several centimeters off the midline | Treat neuropathic components |
| Cancer or phantom limb pain | Place electrodes in skin areas over any painful area | Give nonpainful stimulation to painful area | SCS: at a level appropriate to the pain | Gives paresthesia into the painful area which may lessen pain |
| | | | PNS: on a nerve appropriate to the pain | Treat neuropathic components |
| | | | DBS: PVG or PAG | Treat nociceptive components |
| | | | DBS: VPL or VBM | Treat neuropathic components |
| | | | CS: motor cortex, at a site appropriate for the painful area | Treat neuropathic components |

Table 5 below illustrates various drugs, one or more of which may be delivered in combination with PNFS, either alone or in combination with any of the other stimulation modalities indicated above. Drugs can delivered in combination with PNFS may allow complex or multifocal pain to be better addressed by: diminishing pain by their own action (additive effect), especially if applied to specific sites (patches, intrathecal, epidural); augmenting or magnifying the benefits of electrical stimulation; addressing certain types or locations of pain, such as morphine for nociceptive pain, or local anesthetics to block some nerves.

TABLE 5

| Drug | Delivery Site and Mechanism | Reason for Delivering |
|---|---|---|
| Opioid | Lumbar intrathecal space Systemic (oral, IV, fentanyl patch) Subcutaneous axial back (Permeable membrane catheter) | Treat nociceptive aspects of pain |

TABLE 5-continued

| Drug | Delivery Site and Mechanism | Reason for Delivering |
|---|---|---|
| | Intracerebroventricular Intraparenchymal Local peripheral administration | |
| δ opioid | Systemic, ICV, IP, Local peripheral administration | Synergistic with high frequency stimulation |
| μ opioid | Systemic, ICV, IP, Local peripheral administration | Synergistic with low frequency stimulation |
| Cannabinoid | Lumbar intrathecal space Systemic (oral, IV) Subcutaneous axial back (Permeable membrane catheter) Intracerebroventricular Intraparenchymal Local peripheral administration | Treat nociceptive aspects of pain |
| Local anesthetic (e.g. Bupivacaine) | Lumbar intrathecal Epidural Lumbar sympathetic chain Vertebral disc Facet joint Patch infusion into axial back subcutaneous tissue Local peripheral administration | Additive effect for neuropathic pain |
| Baclofen (GABA agonist) | Systemic Lumbar intrathecal Local peripheral administration | Potentiates neurostimulation |
| Adenosine | Systemic Lumbar intrathecal Local peripheral administration | Potentiates neurostimulation |
| α - adrenergic agonists (e.g. Clonidine) | Systemic Lumbar intrathecal Vertebral disc Facet joint Local peripheral administration | Potentiates neurostimulation Additive effect for neuropathic pain |
| Anti-inflammatory (e.g. NSAIDS, steroids, TNFα blocker) | Systemic Patch infusion into axial back SQ tissue Catheter infusion into SQ tissue Lumbar intrathecal Lumbar epidural Vertebral disc Facet joint Local peripheral administration | Reduce inflammation in addition to stimulation |
| Muscle relaxant | Systemic Patch infusion into axial back SQ tissue Catheter infusion into axial back SQ tissue Local peripheral administration | Relax back muscles in addition to stimulation |
| Antidepressant | Systemic ICV, IP Local peripheral administration | Additive to stimulation |
| Antiepileptic (e.g. Gabapentin) | Systemic ICV, IP Lumbar intrathecal Local peripheral administration | Additive to stimulation |

Various embodiments of the invention have been described. These and other embodiments are within the scope of the following claims.

The invention claimed is:

1. An implantable medical device comprising:
a housing that includes a first major surface and a second major surface, the first major surface and the second major surface separated by a distance, and wherein a length of the first major surface is at least 3 times the distance separating the first major surface and the second major surface;

a plurality of electrodes, wherein a first set of the electrodes is located on the first major surface of the housing, and a second set of the electrodes is located on the second major surface of the housing; and a stimulation generator within the housing configured to deliver electrical stimulation to a patient via the first and second sets of the electrodes.

2. The device of claim 1, wherein the first and second major surfaces of the housing are opposing surfaces of the housing.

3. The device of claim 1, wherein the first and second major surfaces are substantially parallel surfaces.

4. The device of claim 1, wherein the first major surface of the housing is a bottom surface of the housing and the second major surface of the housing is a top surface of the housing.

5. The device of claim 1, wherein the first and second major surfaces are located at different depths within the patient when the device is implanted within the patient.

6. The device of claim 1, wherein at least one of the first set of the electrodes or the second set of electrodes is arranged axially across substantially the entire length of the first or second major surface.

7. The device of claim 1, wherein the first set of electrodes is spatially distributed over substantially the entire first major surface and second set of the electrodes is spatially distributed over substantially the entire second major surface.

8. The device of claim 1, wherein an inter-electrode distance for at least one of the first set of the electrodes or the second set of the electrodes is within a range from approximately 0.1 mm to approximately 5.0 mm.

9. The device of claim 1, wherein at least one of the electrodes is recessed within the housing such that an exterior surface of the electrode is substantially flush with the first or second major surface of the housing.

10. The device of claim 1,
wherein a width of the first major surface of the housing is within a range from approximately 10 mm to approximately 25 mm,
wherein the length of the first major surface of the housing is within a range from approximately 30 mm to approximately 120 mm, and
wherein a thickness of the housing is within a range from approximately 3 mm to approximately 8 mm.

11. The device of claim 1, further comprising:
a processor that controls delivery of electrical stimulation by the stimulation generator; and
a power source that provides power to the processor and the stimulation generator; and
a telemetry module for communication between the processor and an external programmer.

12. The device of claim 1, wherein the housing defines an angle between a first section of the housing and a second section of the housing.

13. The device of claim 12, wherein the first section the housing encloses the stimulation generator and the second section of the housing encloses a power supply.

14. The device of claim 12, wherein the angle is within a range from approximately 10 degrees to approximately 45 degrees.

15. The device of claim 12, wherein the housing comprises a flexible bellows between the first section of the housing and the second section of the housing.

16. The device of claim 1, wherein at least one of the first and second major surfaces is substantially concave or convex.

17. The device of claim 1, wherein the stimulation generator is configured to deliver peripheral nerve field stimulation to the patient via the electrodes.

18. A method comprising:
selecting from among a plurality of electrodes on a housing of an implantable medical device, wherein the housing includes a first surface and a second surface, the first surface and the second surface separated by a distance, and wherein a length of the surface is at least 3 times the distance separating the first surface and the second surface, a first set of the electrodes are located on the first surface, and a second set of the electrodes is located on the second surface; and
delivering electrical stimulation from the implantable medical device to a patient via the selected electrodes.

19. The method of claim 18, wherein the first and second surfaces of the housing are opposing surfaces of the housing.

20. The method of claim 18, wherein the first and second surfaces are substantially parallel surfaces.

21. The method of claim 18, wherein delivering electrical stimulation comprises delivering peripheral nerve field stimulation.

22. The method of claim 21, wherein delivering peripheral nerve field stimulation comprises delivering stimulation to at least one of an intra-dermal, deep dermal, or subcutaneous layer of tissue of the patient.

23. The method of claim 18, wherein delivering electrical stimulation comprises delivering stimulation to a tissue region in which the patient experiences pain, and the implantable medical device implanted within the tissue region.

24. A method comprising:
forming a housing for an implantable medical device, the housing including a first major surface and a second major surface separated by a distance, wherein a length of the first major surface is at least 3 times the distance separating the first major surface and the second major surface;
forming a first set of one or more electrodes on the first major surface of the housing;
forming a second set of one or more electrodes on the second major surface of the housing; and
coupling a stimulation generator to the first and second sets of electrodes.

25. The method of claim 24, wherein the first and second major surfaces of the housing are opposing surfaces of the housing.

26. The method of claim 24, wherein the first and second major surfaces are substantially parallel surfaces.

27. The method of claim 24, wherein forming a first set of one or more electrodes on the first major surface of the housing comprises spatially distributing the first set of electrodes over substantially the entire first major surface, and wherein forming a second set of one or more electrodes on the second major surface of the housing comprises spatially distributing the second set of the electrodes over substantially the entire second major surface.

28. The method of claim 24, wherein forming the first and second sets of electrodes comprises recessing at least one of the electrodes within the housing such that an exterior surface of the electrode is substantially flush with the first or second major surface of the housing.

29. The device of claim 1, wherein the first major surface and the distance between the first major surface and the second major surfaced are sized such that, when implanted within one or more subcutaneous tissue layers, the first major surface and the second major surface face different ones of the subcutaneous layers, and wherein the stimulation generator is configured to deliver peripheral nerve field stimulation to the patient via the electrodes to one or more of the subcutaneous layers.

* * * * *